US012678118B2

(12) United States Patent
Sugahara et al.

(10) Patent No.: US 12,678,118 B2
(45) Date of Patent: Jul. 14, 2026

(54) IMAGE PROCESSING APPARATUS, IMAGE CAPTURING SYSTEM, IMAGE PROCESSING METHOD, AND IMAGE PROCESSING PROGRAM

(71) Applicant: FUJIFILM Corporation, Tokyo (JP)

(72) Inventors: Masataka Sugahara, Kanagawa (JP); Hisatsugu Horiuchi, Kanagawa (JP); Sayaka Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 22 days.

(21) Appl. No.: 18/597,879

(22) Filed: Mar. 6, 2024

(65) Prior Publication Data

US 2024/0298991 A1 Sep. 12, 2024

(30) Foreign Application Priority Data

Mar. 10, 2023 (JP) ................................ 2023-038163

(51) Int. Cl.
*A61B 6/00* (2024.01)
*A61B 6/02* (2006.01)
(Continued)

(52) U.S. Cl.
CPC ............ *A61B 6/5247* (2013.01); *A61B 6/025* (2013.01); *A61B 6/0414* (2013.01); *A61B 6/461* (2013.01);
(Continued)

(58) Field of Classification Search
CPC ..... A61B 6/5247; A61B 6/025; A61B 6/0414; A61B 6/461; A61B 6/502; A61B 8/0825;
(Continued)

(56) References Cited

U.S. PATENT DOCUMENTS

| | | | | |
|---|---|---|---|---|
| 6,459,925 | B1 * | 10/2002 | Nields .................... | A61B 8/467 600/440 |
| 12,076,180 | B2 * | 9/2024 | Ishikawa ................ | A61B 8/466 |

(Continued)

FOREIGN PATENT DOCUMENTS

| | | |
|---|---|---|
| JP | 2009-028381 A | 2/2009 |
| JP | 2012-170718 A | 9/2012 |

*Primary Examiner* — Baisakhi Roy
(74) *Attorney, Agent, or Firm* — Studebaker Brackett PLLC

(57) ABSTRACT

An image processing apparatus includes at least one processor, and the processor is configured to: acquire a synthesized two-dimensional image including information in a depth direction of a breast, the synthesized two-dimensional image being a composite image obtained by synthesizing a plurality of radiation images of the breast imaged in a compression state by a compression member; display the synthesized two-dimensional image; acquire position information indicating a position in the displayed synthesized two-dimensional image; acquire a plurality of ultrasound images of the breast imaged in a compression state by the compression member, the compression state which is considered to be the same as that in capturing the radiation image; and display an ultrasound image for display according to the plurality of ultrasound images with depth information indicating a depth of the breast corresponding to the position indicated by the position information added thereto.

18 Claims, 19 Drawing Sheets

(51) Int. Cl.

| | |
|---|---|
| ***A61B 6/04*** | (2006.01) |
| ***A61B 6/46*** | (2024.01) |
| ***A61B 6/50*** | (2024.01) |
| ***A61B 8/00*** | (2006.01) |
| ***A61B 8/08*** | (2006.01) |

(52) U.S. Cl.

CPC ............ *A61B 6/502* (2013.01); *A61B 8/0825* (2013.01); *A61B 8/461* (2013.01)

(58) Field of Classification Search

CPC ......... A61B 8/461; A61B 6/463; A61B 6/469; A61B 8/469

See application file for complete search history.

(56) References Cited

U.S. PATENT DOCUMENTS

| | | | | |
|---|---|---|---|---|
| 2016/0007944 | A1* | 1/2016 | O'Connor | A61B 8/0825 600/431 |
| 2016/0235380 | A1* | 8/2016 | Smith | A61B 6/463 |
| 2019/0209012 | A1* | 7/2019 | Yoshimoto | A61B 5/0059 |
| 2021/0125334 | A1* | 4/2021 | Lotter | A61B 6/025 |
| 2021/0228170 | A1* | 7/2021 | Fukuda | A61B 6/025 |
| 2021/0228180 | A1* | 7/2021 | Terada | A61B 8/15 |
| 2021/0393225 | A1* | 12/2021 | Morita | A61B 6/466 |
| 2023/0146520 | A1* | 5/2023 | Rong | A61B 8/0825 600/427 |

* cited by examiner

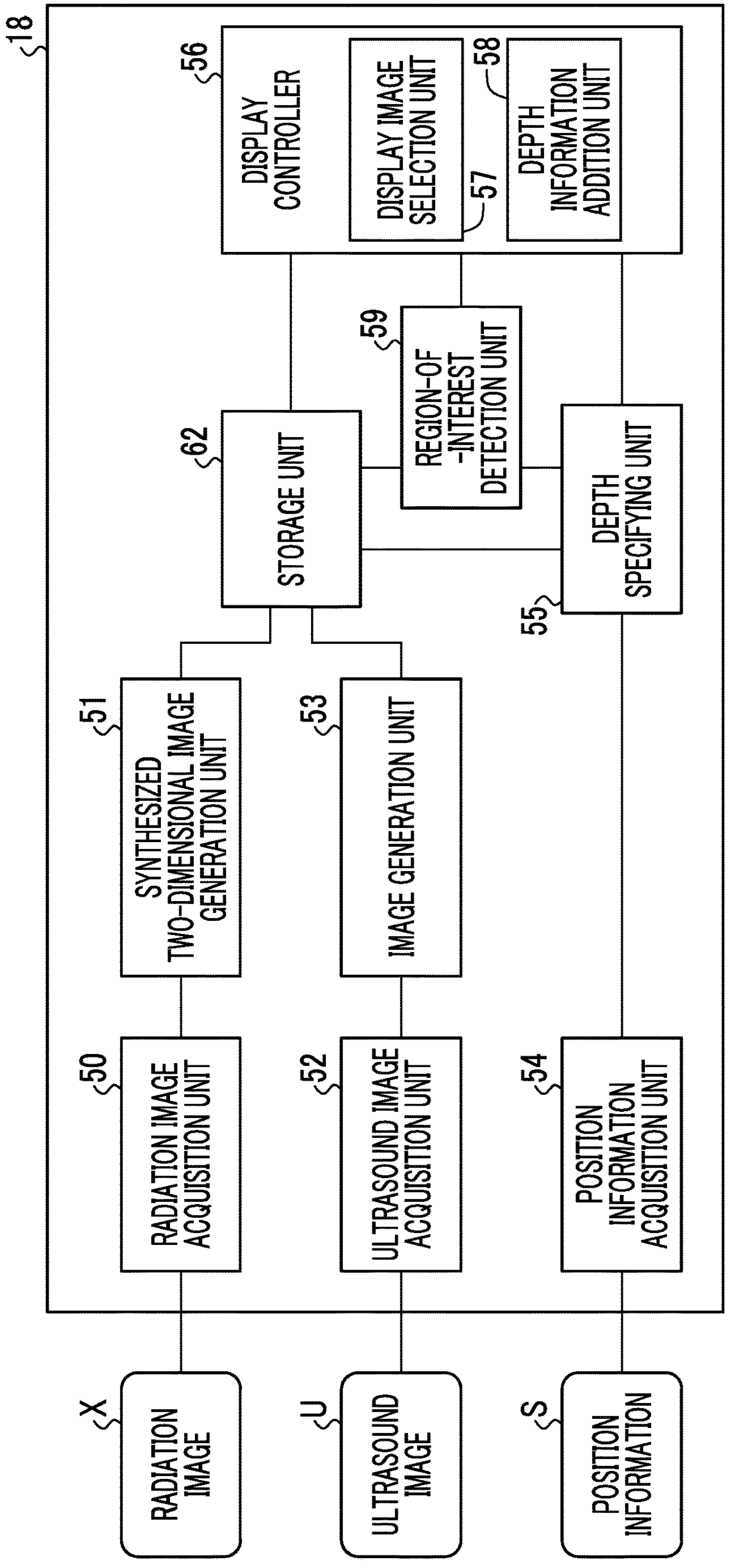

RADIATION
IMAGE — X

RADIATION IMAGE
ACQUISITION UNIT — 50

SYNTHESIZED
TWO-DIMENSIONAL IMAGE
GENERATION UNIT — 51

ULTRASOUND
IMAGE — U

ULTRASOUND IMAGE
ACQUISITION UNIT — 52

IMAGE GENERATION UNIT — 53

POSITION
INFORMATION — S

POSITION
INFORMATION
ACQUISITION UNIT — 54

STORAGE UNIT — 62

REGION-OF
-INTEREST
DETECTION UNIT — 59

DEPTH
SPECIFYING UNIT — 55

DISPLAY
CONTROLLER — 56

DISPLAY IMAGE
SELECTION UNIT — 57

DEPTH
INFORMATION
ADDITION UNIT — 58

| No. | SCORE | TYPE |
|---|---|---|
| 1 | 70.5 | TUMOR |
| 2 | 34.8 | CALCIFICATION |

A-A LINE CROSS SECTION

90

LA

D

ULTRASOUND IMAGE
(THREE-DIMENSIONAL ULTRASOUND IMAGE)

98

B-B LINE CROSS SECTION

D

LB

94

RADIATION IMAGE
(SYNTHESIZED TWO-DIMENSIONAL IMAGE)

80

CA

CB

A

B 87A
87B
87D

D

LC

94

L

68

88

IMAGE PROCESSING APPARATUS, IMAGE CAPTURING SYSTEM, IMAGE PROCESSING METHOD, AND IMAGE PROCESSING PROGRAM

CROSS REFERENCE TO RELATED APPLICATIONS

This application claims priority from Japanese Application No. 2023-038163, filed on Mar. 10, 2023, the entire disclosure of which is incorporated herein by reference.

BACKGROUND

1. Technical Field

The present disclosure relates to an image processing apparatus, an image capturing system, an image processing method, and a non-transitory storage medium storing an image processing program.

2. Related Art

A radiography apparatus is known that irradiates a subject, such as the breast of an examinee, with radiation emitted from a radiation source and detects the radiation transmitted through the subject with a radiation detector to capture a radiation image.

Further, an ultrasonography apparatus is known that captures an ultrasound image of the breast by causing an ultrasound probe to perform scanning along the breast of the examinee to scan the breast with ultrasound.

JP2009-28381A and JP2012-170718A disclose apparatuses that can capture both a radiation image and an ultrasound image of the breast. In JP2009-28381A and JP2012-170718A, the radiation image and the ultrasound image are captured in a state in which the breast is compressed.

By the way, in the diagnosis of a breast, it is preferable to perform three-dimensional observation of a breast tissue. In order to observe three-dimensional structures, a synthesized two-dimensional image synthesized from a plurality of radiation images is used for observation. Furthermore, a radiation image such as a synthesized two-dimensional image and an ultrasound image are displayed side by side, and the image is interpreted while comparing the two images. However, in the related art, it is sometimes difficult to compare a synthesized two-dimensional image with an ultrasound image, and therefore it is sometimes difficult to recognize the three-dimensional structure of a breast tissue.

SUMMARY

The present disclosure has been made in consideration of the above-mentioned circumstances, and an object of the present disclosure is to provide an image processing apparatus, an image capturing system, an image processing method, and a non-transitory storage medium storing an image processing program that make it easier for a user to compare a synthesized two-dimensional image synthesized from radiation images with an ultrasound image.

In order to achieve the above object, according to a first aspect of the present disclosure, there is provided an image processing apparatus comprising at least one processor, in which the processor may be configured to: acquire a synthesized two-dimensional image including information in a depth direction of a breast, the synthesized two-dimensional image being a composite image obtained by synthesizing a plurality of radiation images of the breast imaged in a compression state by a compression member; display the synthesized two-dimensional image; acquire position information indicating a position in the displayed synthesized two-dimensional image; acquire a plurality of ultrasound images of the breast imaged in a compression state by the compression member, the compression state which is considered to be the same as that in capturing the radiation image; and display an ultrasound image for display according to the plurality of ultrasound images with depth information indicating a depth of the breast corresponding to the position indicated by the position information added thereto.

According to a second aspect of the present disclosure, in the image processing apparatus according to the first aspect, the ultrasound image for display may be any of the plurality of ultrasound images, and may be at least one of: a first cross-sectional ultrasound image that is a cross-sectional image in a direction intersecting an imaging table on which the breast is placed; a second cross-sectional ultrasound image that is synthesized from the plurality of ultrasound images and is a cross-sectional image in a direction intersecting the imaging table and the first cross-sectional ultrasound image; a third cross-sectional image that is synthesized from the plurality of ultrasound images and is a cross-sectional image parallel to the imaging table; or a three-dimensional ultrasound image that is synthesized from the plurality of ultrasound images and corresponds to a cross section parallel to the imaging table.

According to a third aspect of the present disclosure, in the image processing apparatus according to the second aspect, the processor may be configured to display, as the ultrasound image for display to which the depth information is added, at least one of the third cross-sectional image or the three-dimensional ultrasound image corresponding to a cross section according to a position of the depth of the breast corresponding to the position indicated by the position information.

According to a fourth aspect of the present disclosure, in the image processing apparatus according to the first aspect, the processor may be configured to: detect a first region of interest from the synthesized two-dimensional image; display, on the synthesized two-dimensional image, first region-of-interest information indicating the first region of interest; acquire position information indicating a position of the first region of interest; detect a second region of interest from a region corresponding to a vicinity of the first region of interest in the ultrasound image for display; and display, on the ultrasound image for display, second region-of-interest information indicating the second region of interest.

According to a fifth aspect of the present disclosure, in the image processing apparatus according to the first aspect, the radiation image may be a radiation image obtained by tomosynthesis imaging, and the processor may be configured to: acquire a tomographic image obtained by reconstructing the radiation image; detect a first region of interest from the tomographic image; display, on the synthesized two-dimensional image, a corresponding region corresponding to the first region of interest; acquire position information indicating a position of the corresponding region on the synthesized two-dimensional image; detect a second region of interest from a region corresponding to a vicinity of the first region of interest in the ultrasound image for display according to the position indicated by the position information; and display, on the ultrasound image for display, second region-of-interest information indicating the second region of interest.

According to a sixth aspect of the present disclosure, in the image processing apparatus according to the fourth or fifth aspect, the processor may be configured to: in a case in which a plurality of the second regions of interest are detected, display a list of scores indicating a degree of suspicion of each second region of interest; and in a case in which a second region of interest designated from the list is received, display information indicating the received second region of interest on the ultrasound image for display.

According to a seventh aspect of the present disclosure, in the image processing apparatus according to the first aspect, the processor may be configured to display a line serving as an indicator at a position corresponding to the depth as the depth information to be added to the ultrasound image for display.

According to an eighth aspect of the present disclosure, in the image processing apparatus according to the first aspect, the processor may be configured to: display a movable cross section line on the synthesized two-dimensional image to designate a position of a cross section; and display the ultrasound image for display representing the cross section designated by the cross section line.

According to a ninth aspect of the present disclosure, in the image processing apparatus according to the first aspect, the processor may be configured to: detect a first region of interest from the synthesized two-dimensional image; display, on the synthesized two-dimensional image, first region-of-interest information indicating the first region of interest; and acquire a position of the first region of interest as the position information.

According to a tenth aspect of the present disclosure, in the image processing apparatus according to the ninth aspect, the processor may be configured to: display, on the synthesized two-dimensional image, a cross section line passing through a centroid position or a maximum density position of the region of interest; and display the ultrasound image for display representing the cross section designated by the cross section line.

According to an eleventh aspect of the present disclosure, in the image processing apparatus according to the tenth aspect, the processor may be configured to display, as the cross section line, two cross section lines with the centroid position or the maximum density position of the first region of interest as an intersection.

According to a twelfth aspect of the present disclosure, in the image processing apparatus according to the ninth aspect, the processor may be configured to: detect a second region of interest from the ultrasound image for display representing a cross section designated by a cross section line; and display, on the ultrasound image for display, second region-of-interest information indicating the detected second region of interest.

According to a thirteenth aspect of the present disclosure, in the image processing apparatus according to the first aspect, the radiation image may be a radiation image obtained by tomosynthesis imaging, and the processor may be configured to: acquire a tomographic image obtained by reconstructing the radiation image; detect a first region of interest from the tomographic image; acquire position information indicating a position corresponding to the first region of interest on the synthesized two-dimensional image; display, on the synthesized two-dimensional image, a cross section line passing through a centroid position or a maximum density position of the first region of interest; display the ultrasound image for display representing a cross section designated by the cross section line; detect a second region of interest from the ultrasound image for display; and display, on the ultrasound image for display, second region-of-interest information indicating the second region of interest.

According to a fourteenth aspect of the present disclosure, in the image processing apparatus according to the thirteenth aspect, the processor may be configured to: in a case in which a plurality of the second regions of interest are detected from the ultrasound image for display, display a list of scores indicating a degree of suspicion of each second region of interest; and in a case in which a second region of interest designated from the list is received, display the second region-of-interest information indicating the received second region of interest on the ultrasound image for display.

According to a fifteenth aspect of the present disclosure, in the image processing apparatus according to the first aspect, the processor may be configured to determine that, in a case in which capturing of the ultrasound image and capturing of the radiation image are continuously performed while the breast is kept in the compression state by the compression member, a compression state of the breast in the capturing of the ultrasound image and a compression state of the breast in the capturing of the radiation image are the same.

According to a sixteenth aspect of the present disclosure, in the image processing apparatus according to the first aspect, the processor may be configured to determine that, in a case in which compression conditions for putting the breast into the compression state are the same, a compression state of the breast in capturing of the ultrasound image and a compression state of the breast in capturing of the radiation image are the same.

According to a seventeenth aspect of the present disclosure, in the image processing apparatus according to the first aspect, the processor may be configured to determine that, in a case in which states of the breast in the compression state are the same, a compression state of the breast in capturing of the ultrasound image and a compression state of the breast in capturing of the radiation image are the same.

According to an eighteenth aspect of the present disclosure, in the image processing apparatus according to the first aspect, the processor may be configured to further determine that, in a case in which a state of the breast itself in capturing of the plurality of ultrasound images and a state of the breast itself in capturing of the radiation image are considered to be the same, a compression state of the breast in the capturing of the ultrasound image and a compression state of the breast in the capturing of the radiation image are the same.

In addition, in order to achieve the above object, according to a nineteenth aspect of the present disclosure, there is provided an image capturing system comprising: the image processing apparatus according to the aspect of the present disclosure; a radiography apparatus; and an ultrasonography apparatus.

In addition, in order to achieve the above object, according to a twentieth aspect of the present disclosure, there is provided an image processing method executed by a computer, the method comprising: acquiring a synthesized two-dimensional image including information in a depth direction of a breast, the synthesized two-dimensional image being a composite image obtained by synthesizing a plurality of radiation images of the breast imaged in a compression state by a compression member; displaying the synthesized two-dimensional image; acquiring position information indicating a position in the displayed synthesized two-dimensional image; acquiring a plurality of ultrasound images of the breast imaged in a compression state by the compression member, the compression state which is considered to be the same as that in capturing the radiation image; and displaying an ultrasound image for display according to the plurality of ultrasound images with depth information indicating a depth of the breast corresponding to the position indicated by the position information added thereto.

In addition, in order to achieve the above object, according to a twenty-first aspect of the present disclosure, there is provided a non-transitory storage medium storing an image processing program for causing a computer to execute image processing: the image processing comprising: acquiring a synthesized two-dimensional image including information in a depth direction of a breast, the synthesized two-dimensional image being a composite image obtained by synthesizing a plurality of radiation images of the breast imaged in a compression state by a compression member; displaying the synthesized two-dimensional image; acquiring position information indicating a position in the displayed synthesized two-dimensional image; acquiring a plurality of ultrasound images of the breast imaged in a compression state by the compression member, the compression state which is considered to be the same as that in capturing the radiation image; and displaying an ultrasound image for display according to the plurality of ultrasound images with depth information indicating a depth of the breast corresponding to the position indicated by the position information added thereto.

According to the aspects of the present disclosure, it is possible to make it easier for a user to compare a synthesized two-dimensional image synthesized from radiation images with an ultrasound image.

BRIEF DESCRIPTION OF THE DRAWINGS

FIG. 11 is a functional block diagram showing an example of the configuration of an image processing apparatus according to a second embodiment.

DESCRIPTION OF EMBODIMENTS

Embodiments of the present invention will be described in detail below with reference to the drawings. Note that the present embodiment does not limit the present invention.

First Embodiment

In the present embodiment, an aspect in which a compression force of compressing the entire breast is an example of a force of compressing a breast of the present disclosure will be described.

Figure 1:
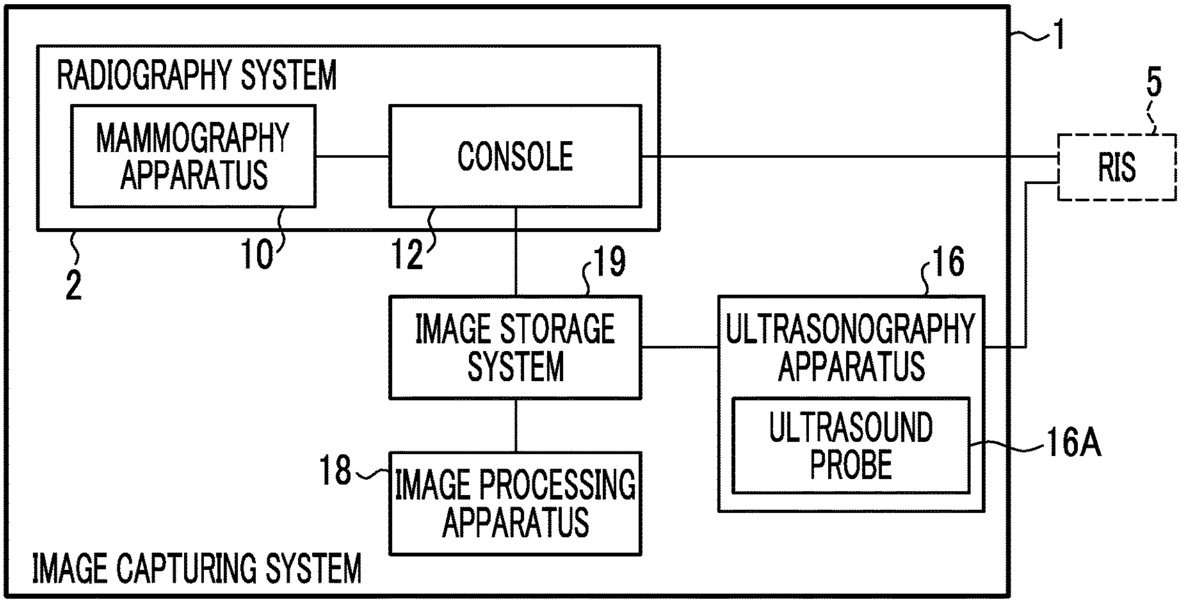
FIG. 1 is a configuration diagram schematically showing an example of the overall configuration of an image capturing system according to a first embodiment.

First, an example of the overall configuration of a medical imaging system according to the present embodiment will be described. FIG. 1 is a configuration diagram showing an example of the overall configuration of an image capturing system 1 according to the present embodiment.

As shown in FIG. 1, the image capturing system 1 according to the present embodiment comprises a radiography system 2, an ultrasonography apparatus 16, an image processing apparatus 18, and an image storage system 19.

First, the configuration of the radiography system 2 will be described. The radiography system 2 includes a mammography apparatus 10 and a console 12.

The mammography apparatus 10 of the present embodiment is an apparatus that uses a breast of the examinee as a subject and captures a radiation image of the breast by irradiating the breast with radiation R (for example, X-rays). Note that the mammography apparatus 10 may be an apparatus that images the breast of the examinee in a state in which the examinee is sitting on a chair (including a wheelchair) or the like (sitting state) in addition to a state in which the examinee is standing (standing state).

Figure 2:
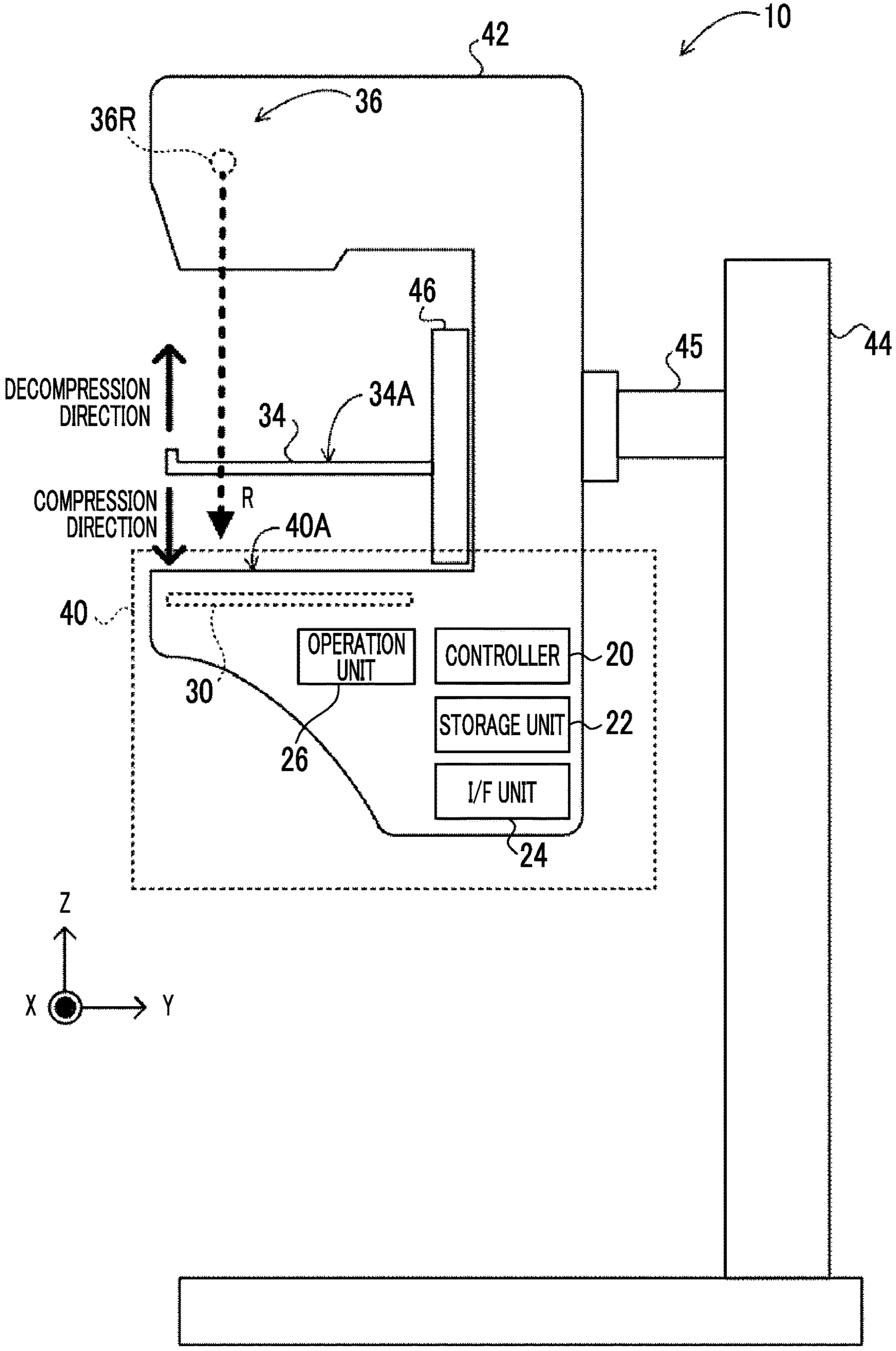
FIG. 2 is a side view showing an example of the appearance of a mammography apparatus according to the first embodiment.

FIG. 2 is a side view showing an example of the appearance of the mammography apparatus 10 of the present embodiment. In addition, FIG. 2 is a side view showing the mammography apparatus 10 as viewed from the right side of an examinee. As shown in FIG. 2, the mammography apparatus 10 comprises a radiation source 36R, a radiation detector 30, an imaging table 40 disposed between the radiation source 36R and the radiation detector 30, and a compression member 34 that compresses the breast between the compression member 34 and the imaging table 40.

The imaging table 40 comprises a controller 20, a storage unit 22, an interface (I/F) unit 24, an operation unit 26, and the radiation detector 30. The controller 20 controls an overall operation of the mammography apparatus 10 in accordance with the control of the console 12. The controller 20 comprises a central processing unit (CPU), a read-only memory (ROM), a random-access memory (RAM), and the like (not shown). The ROM stores, in advance, various programs, including a program for performing control related to radiation image capturing, which is executed by the CPU. The RAM transitorily stores various types of data.

Image data of a radiation image and various other types of information are stored in the storage unit 22. The storage unit 22 is realized by, for example, a storage medium such as a hard disk drive (HDD), a solid-state drive (SSD), and a flash memory. Note that, hereinafter, "image data of a radiation image" is simply referred to as a "radiation image". Similarly, "image data of an ultrasound image" is simply referred to as an "ultrasound image".

The I/F unit 24 communicates various types of information with the console 12 through wired communication or wireless communication. Specifically, the I/F unit 24 receives information regarding the control of the mammography apparatus 10 from the console 12. In addition, the I/F unit 24 transmits a radiation image to the console 12.

The operation unit 26 is a part provided on the imaging table 40 or the like and operable by a user with a hand, a foot, or the like, and is, for example, a switch, a button, a touch panel, or the like. Further, for example, the operation unit 26 may receive a voice input from the user.

The radiation detector 30 is disposed inside the imaging table 40 and detects the radiation R transmitted through the breast which is the subject. In the mammography apparatus 10 of the present embodiment, in a case in which imaging is performed, the breast of the examinee is positioned on an imaging surface 40A of the imaging table 40 by a user such as a doctor or a radiology technician. For example, the imaging surface 40A and the like with which the breast of the examinee comes into contact are made of carbon or the like in terms of the transmittance and intensity of the radiation R.

The radiation detector 30 detects the radiation R transmitted through the breast of the examinee and the imaging table 40, generates a radiation image based on the detected radiation R, and outputs the generated radiation image. The type of the radiation detector 30 of the present embodiment is not particularly limited. For example, the radiation detector 30 may be an indirect conversion type radiation detector that converts the radiation R into light and converts the converted light into electric charges, or may be a direct conversion type radiation detector that directly converts the radiation R into electric charges.

The radiation source 36R is provided in a radiation emitting unit 36. As shown in FIG. 2, the radiation emitting unit 36 is provided on the arm part 42 together with the imaging table 40 and a compression unit 46. In addition, as shown in FIG. 2, the mammography apparatus 10 of the present embodiment comprises the arm part 42, a base 44, and a shaft part 45. The arm part 42 is held by the base 44 so as to be movable in an up-down direction (Z-axis direction). The shaft part 45 connects the arm part 42 to the base 44. Further, the arm part 42 can be relatively rotated with respect to the base 44, using the shaft part 45 as a rotation axis.

The mammography apparatus 10 of the present embodiment can perform so-called tomosynthesis imaging. Tomosynthesis imaging is an imaging method in which radiation irradiation angles for a subject (breast in the present embodiment) are varied, and a radiation image (projection image) is captured for each irradiation angle. In a case in which tomosynthesis imaging is performed, by rotating the arm part 42, the radiation source 36R of the radiation emitting unit 36 is moved to each of a plurality of irradiation positions having different irradiation angles (projection angles). For example, the radiation source 36R is moved to an irradiation position where the irradiation angle is different by a predetermined angle θ. In other words, the radiation source 36R is moved to a position where an incidence angle of the radiation R with respect to a detection surface of the radiation detector 30 is different. At each irradiation position, radiation R is emitted from the radiation source 36R according to instructions from the console 12, and a radiation image (projection image) is captured by the radiation detector 30. In this way, in tomosynthesis imaging, a plurality of radiation images (projection images) are obtained according to the number of the plurality of irradiation positions.

A mammography apparatus that enables tomosynthesis imaging is not limited to the aspect of the mammography apparatus 10 of the present embodiment, which comprises one radiation source 36R and in which the radiation source 36R is moved to each irradiation position and a radiation image (projection image) is captured at each irradiation position. For example, a mammography apparatus for performing tomosynthesis imaging may be a mammography apparatus in which a radiation source 36R is provided for each irradiation position, and the entire apparatus comprises a plurality of radiation sources 36R.

Further, as shown in FIG. 2, the compression member 34 is attached to the compression unit 46. The compression unit 46 and the arm part 42 can be relatively rotated with respect to the base 44 separately, using the shaft part 45 as a rotation axis. In the present embodiment, gears (not shown) are provided in each of the shaft part 45, the arm part 42, and the compression unit 46. Each gear is switched between an engaged state and a disengaged state to connect each of the arm part 42 and the compression unit 46 to the shaft part 45. One or both of the arm part 42 and the compression unit 46 connected to the shaft part 45 are rotated integrally with the shaft part 45.

The compression member 34 of the present embodiment is a plate-shaped member, and is moved in the up-down direction (Z-axis direction) by a compression plate drive part (not shown) provided in the compression unit 46 to compress the breast of the examinee between the compression member 34 and the imaging table 40. As shown in FIG. 2, regarding the movement direction of the compression member 34, the direction in which the breast is compressed, in other words, the direction in which the compression member 34 becomes closer to the imaging surface 40A is referred to as a "compression direction" and the direction in which the compression of the breast is released, in other words, the direction in which the compression member 34 becomes closer to the radiation emitting unit 36 is referred to as a "decompression direction".

It is preferable that the compression member 34 is optically transparent in order to check positioning or a compression state in the compression of the breast. In addition, the compression member 34 is made of a material having high transmittance for the radiation R. Further, it is desirable that the compression member 34 is made of a material that facilitates the transmission of ultrasonic waves from an ultrasound probe 16A (see FIG. 3, details will be described later) of the ultrasonography apparatus 16. Examples of the material forming the compression member 34 include resins such as polymethylpentene, polycarbonate, acrylic, or polyethylene terephthalate. In particular, polymethylpentene is suitable as the material forming the compression member 34 since it has low rigidity, high elasticity, and high flexibility and has suitable values for acoustic impedance that affects the reflectance of ultrasonic waves and an attenuation coefficient that affects the attenuation of ultrasonic waves. The member forming the compression member 34 is not limited to the present embodiment. For example, the member forming the compression member 34 may be a film-like member.

Note that the compression member 34 is not limited to one that compresses the entire breast, but may be one that compresses a part of the breast. In other words, the compression member 34 may be smaller than the breast. As such a compression member 34, for example, a compression member 34 used for so-called spot imaging, in which a radiation image is captured of only a region where a lesion is present, is known.

On the other hand, the console 12 of the present embodiment has a function of controlling the mammography apparatus 10 using an imaging order and various types of information acquired from a radiology information system (RIS) 5 or the like through a wireless communication local area network (LAN), instructions input by the user using an operation unit 66 or the like, and the like. Furthermore, the console 12 transmits the radiation image captured by the mammography apparatus 10 to the image storage system 19 through wireless communication or wired communication. The console 12 of the present embodiment is, for example, a server computer.

Next, the ultrasonography apparatus 16 will be described. As shown in FIG. 1, the ultrasonography apparatus 16 of the present embodiment comprises an ultrasound probe 16A. The ultrasonography apparatus 16 is a so-called handheld type ultrasonography apparatus that captures an ultrasound image of the breast of the examinee as a subject by scanning the ultrasound probe 16A by a user.

The ultrasound probe 16A is moved along an upper surface 34A (see FIG. 2, a surface opposite to the surface that comes into contact with the breast of the examinee) of the compression member 34 by the user and scans the breast with ultrasound to acquire an ultrasound image of the breast. Specifically, in a case in which an ultrasound imaging is performed, the ultrasound probe 16A is moved by the user along the upper surface 34A of the compression member 34 in a state in which an acoustic matching member (not shown), such as echo jelly, is applied onto the upper surface 34A of the compression member 34.

The ultrasound probe 16A comprises a plurality of ultrasound transducers (not shown) which are one-dimensionally or two-dimensionally arranged. Each of the ultrasound transducers transmits ultrasonic waves based on an applied drive signal, receives ultrasound echoes, and outputs a received signal. Each of the plurality of ultrasound transducers is composed of, for example, a transducer in which electrodes are formed at both ends of a piezoelectric material (piezoelectric body) such as a piezoelectric ceramic represented by lead (Pb) zirconate titanate (PZT) or a polymer piezoelectric element represented by polyvinylidene difluoride (PVDF). In a case in which a pulsed or continuous wave drive signal is transmitted to apply a voltage to the electrodes of the transducer, the piezoelectric body is expanded and contracted. Pulsed or continuous ultrasonic waves are generated from each transducer by the expansion and contraction and the ultrasonic waves are synthesized to form an ultrasound beam. Further, each transducer receives the propagated ultrasonic waves and is then expanded and contracted to generate an electric signal. The electric signal is output as an ultrasound received signal and is input to the main body (not shown) of the ultrasonography apparatus 16 through a cable (not shown).

The ultrasound image captured by the ultrasonography apparatus 16 is transmitted to the image storage system 19 through wireless communication or wired communication.

Next, the image storage system 19 will be described. The image storage system 19 is a system that stores the radiation image captured by the radiography system 2 and the ultrasound image captured by the ultrasonography apparatus 16. The image storage system 19 is connected to each of the console 12 and the ultrasonography apparatus 16 through wireless communication or wired communication. The image storage system 19 extracts an image corresponding to a request from, for example, the console 12, the ultrasonography apparatus 16, and other interpretation devices (not shown) from the stored radiation images and ultrasound images and transmits the extracted image to the apparatus which is the request source. A specific example of the image storage system 19 is a picture archiving and communication system (PACS).

Next, the image processing apparatus 18 will be described. The image processing apparatus 18 has a function of acquiring each of a radiation image captured by the radiography system 2 and an ultrasound image captured by the ultrasonography apparatus 16 from the image storage system 19 and performing predetermined image processing.

Figure 3:
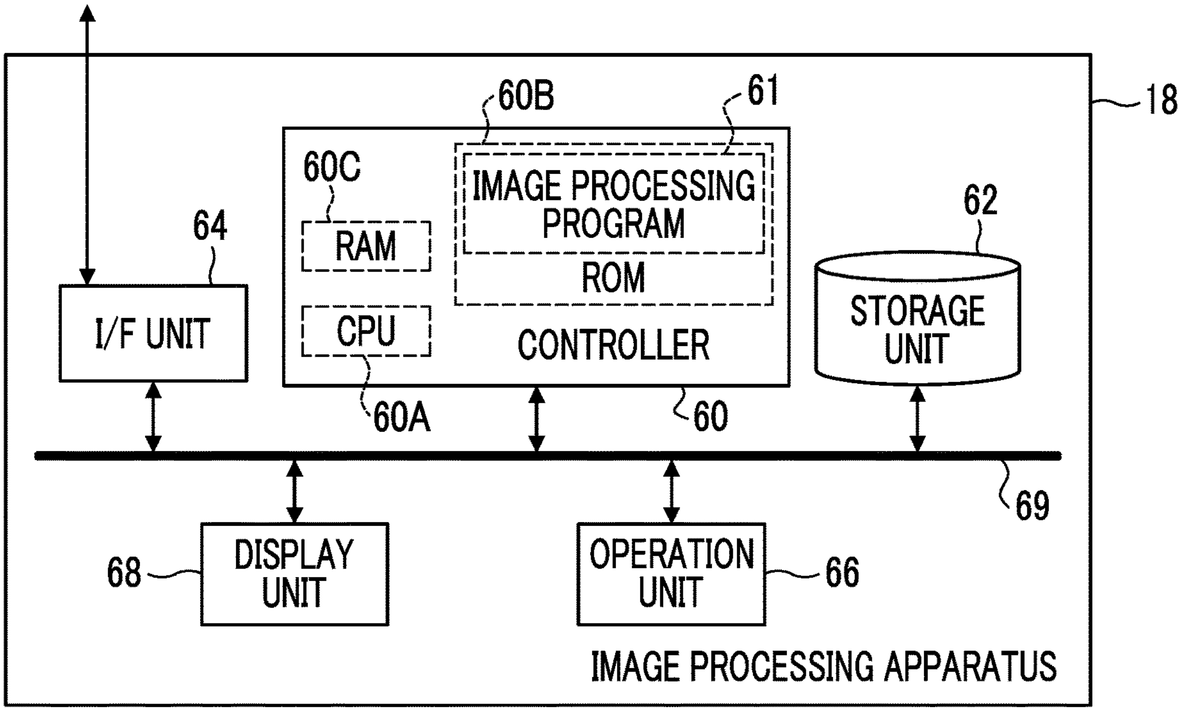
FIG. 3 is a block diagram showing an example of the configuration of an image processing apparatus according to the first embodiment.

FIG. 3 is a block diagram showing an example of the configuration of the image processing apparatus 18. As shown in FIG. 3, the image processing apparatus 18 comprises a controller 60, a storage unit 62, an I/F unit 64, an operation unit 66, and a display unit 68. The controller 60, the storage unit 62, the I/F unit 64, the operation unit 66, and the display unit 68 are connected to each other through a bus 69 such as a system bus or a control bus, such that they can exchange various types of information with each other.

The controller 60 of the present embodiment controls the overall operation of the image processing apparatus 18. The controller 60 comprises a CPU 60A, a ROM 60B, and a RAM 60C. The ROM 60B stores in advance various programs including an image processing program 61 to be described later, which is executed by the CPU 60A. The RAM 60C transitorily stores various types of data.

The storage unit 62 stores, for example, the radiation image, the ultrasound image, and various other types of information acquired from the image storage system 19. Specific examples of the storage unit 62 include an HDD, an SSD, and the like.

The operation unit 66 is used by the user to input, for example, instructions or various types of information regarding image processing. Note that, the operation unit 66 is not particularly limited, and examples of the operation unit 66 include various switches, a touch panel, a touch pen, a mouse, and the like. The display unit 68 displays various types of information. Note that, the operation unit 66 and the display unit 68 may be integrated into a touch panel display.

The I/F unit 64 communicates radiation images, ultrasound images, and various types of information with the image storage system 19 through wireless communication or wired communication.

Figure 4:
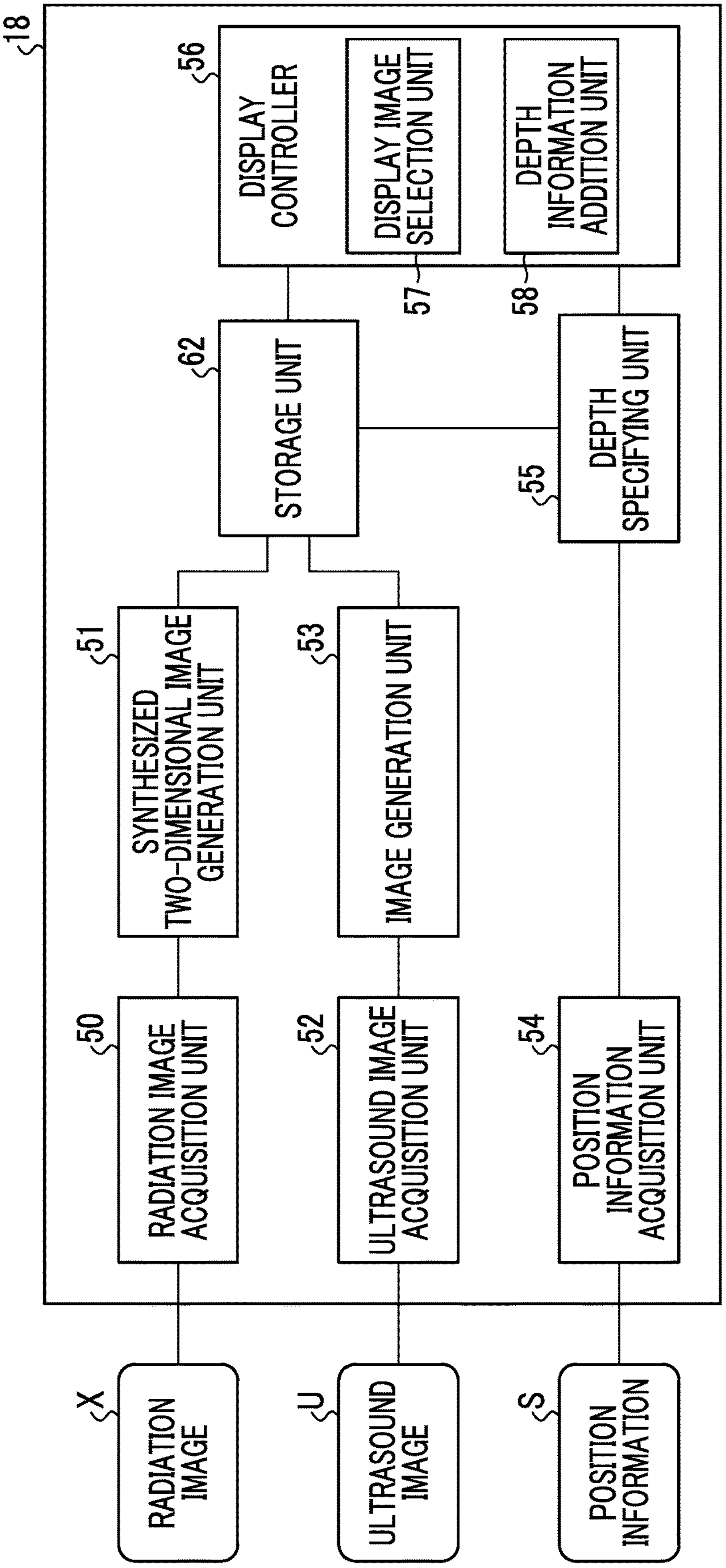
FIG. 4 is a functional block diagram showing an example of the configuration of the image processing apparatus according to the first embodiment.

FIG. 4 is a functional block diagram showing an example of the functions of the image processing apparatus 18. The image processing apparatus 18 comprises a radiation image acquisition unit 50, a synthesized two-dimensional image generation unit 51, an ultrasound image acquisition unit 52, an image generation unit 53, a position information acquisition unit 54, a depth specifying unit 55, and a display controller 56. As an example, in the image processing apparatus 18 according to the present embodiment, the CPU 60A of the controller 60 executes the image processing program 61, and thereby the CPU 60A functions as the radiation image acquisition unit 50, the synthesized two-dimensional image generation unit 51, the ultrasound image acquisition unit 52, the image generation unit 53, the position information acquisition unit 54, the depth specifying unit 55, and the display controller 56.

The radiation image acquisition unit 50 has a function of acquiring a radiation image X. In addition, as an example, the radiation image X of the present embodiment is a series of radiation images (a plurality of projection images) obtained by tomosynthesis imaging in the mammography apparatus 10. In the present embodiment, in a case in which an image display instruction input by the user through the operation unit 66 is received, the radiation image acquisition unit 50 acquires a radiation image X (a plurality of projection images) of the breast of a specific subject designated by the image display instruction from the image storage system 19 via the I/F unit 64. In the present embodiment, there are a plurality of types of radiation images, such as a projection image captured at each irradiation position in tomosynthesis imaging and a synthesized two-dimensional image obtained by synthesizing the radiation images. However, in a case of being used as a general term without limiting the type, it may simply be referred to as a "radiation image". The radiation image acquisition unit 50 outputs the acquired radiation image X to the synthesized two-dimensional image generation unit 51.

The synthesized two-dimensional image generation unit 51 has a function of generating a synthesized two-dimensional image from the radiation image X. Note that the method by which the synthesized two-dimensional image generation unit 51 generates a synthesized two-dimensional image from the radiation image X, that is, a plurality of projection images is not particularly limited, and a known method can be used. For example, there is a method of reconstructing the radiation image X, which are a plurality of projection images, to generate a plurality of tomographic images and combining the plurality of generated tomographic images to generate a synthesized two-dimensional image.

Figure 5:
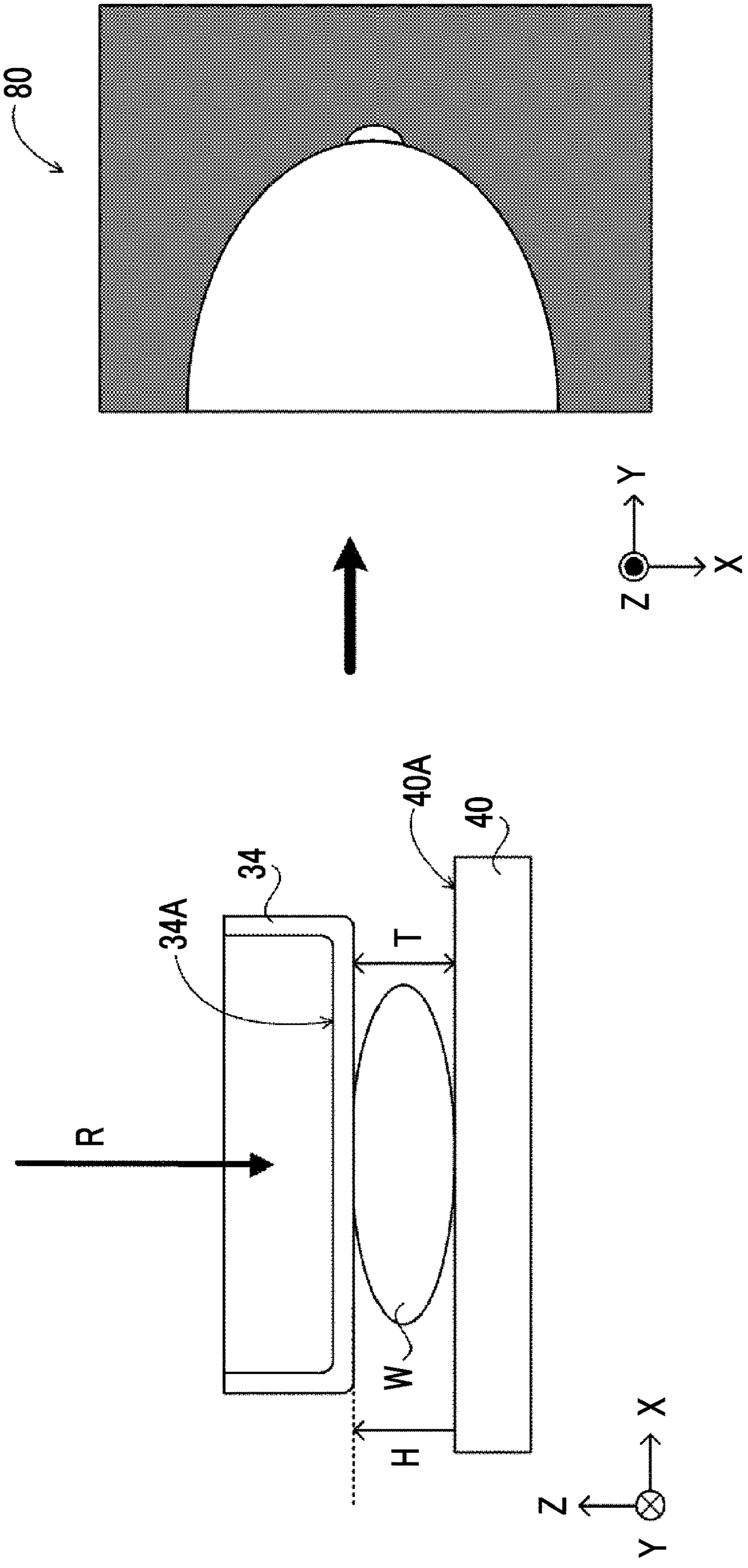
FIG. 5 is a diagram for describing a height in a synthesized two-dimensional image.

The synthesized two-dimensional image of radiation generated by the known method in this way is an image of a cross section that can be considered to be parallel to the imaging surface 40A of the imaging table 40, and includes information in a height direction of the breast. Specifically, as shown in FIG. 5, a synthesized two-dimensional image 80 is an image that can be considered to be parallel to the imaging surface 40A and is a two-dimensional image having XY coordinates in FIG. 5. Further, each pixel of the synthesized two-dimensional image 80 has information in the height direction from the imaging surface 40A of the imaging table 40, specifically, information indicating a height H shown in FIG. 5. In this way, in general, the synthesized two-dimensional image 80 has information indicating the height H with respect to the imaging surface 40A of the imaging table 40.

Figure 6:
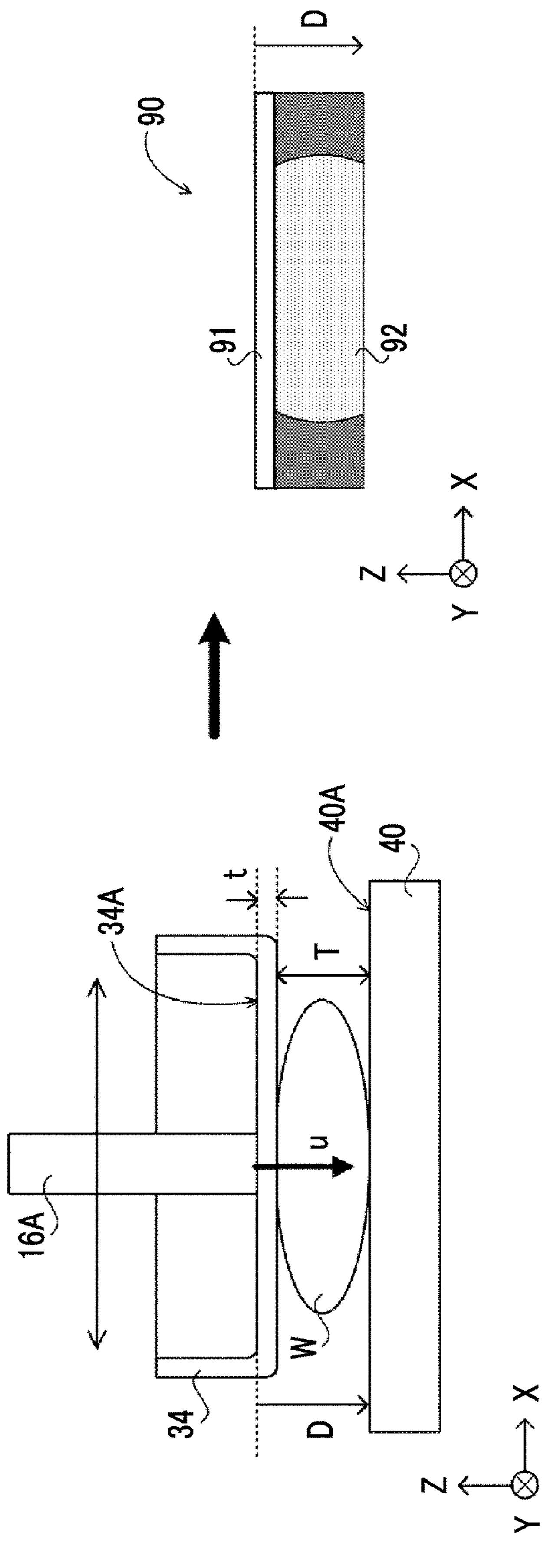
FIG. 6 is a diagram for describing a depth in an ultrasound image.

On the other hand, in a case of capturing an ultrasound image, as shown in FIG. 6, as described above, the upper surface 34A of the compression member 34 is scanned with the ultrasound probe 16A, and ultrasonic waves u are transmitted toward a breast W from the ultrasound probe 16A. For example, in the example shown in FIG. 6, the ultrasound probe 16A is scanned in a left-right direction of the breast W (X direction in FIG. 6) to capture the ultrasound image 90, and a plurality of ultrasound images 90 are captured while shifting the position of the breast W in a front-rear direction (Y direction in FIG. 6). In this case, as shown in FIG. 6, each ultrasound image 90 obtained by the imaging is a cross-sectional image in a direction intersecting the imaging table 40 (left-right direction of the breast W). In order to distinguish the ultrasound image 90 from ultrasound images of other cross sections, in the present embodiment, the ultrasound image 90 is referred to as a first cross-sectional ultrasound image 90.

In order to transmit the ultrasonic waves u from the upper surface 34A of the compression member 34, in the first cross-sectional ultrasound image 90, attention is paid to information in a depth direction from the compression member 34 to the imaging table 40. For example, in the first cross-sectional ultrasound image 90, a position of an internal structure of the breast W is specified by a depth D from the upper surface 34A of the compression member 34 toward the imaging surface 40A of the imaging table 40.

In this way, in a case in which the ultrasound image U requires information in the depth direction but the synthesized two-dimensional image 80 has information in the height direction, the synthesized two-dimensional image generation unit 51 of the present embodiment converts the information in the height direction of the synthesized two-dimensional image 80 into information in the depth direction. Note that, as shown in FIG. 6, the first cross-sectional ultrasound image 90 includes a compression member image 91 formed by the member on the upper surface 34A side of the compression member 34, and a breast image 92 formed by the breast W. Therefore, the synthesized two-dimensional image generation unit 51 of the present embodiment converts information in the height direction of the synthesized two-dimensional image 80 into information in the depth direction using a thickness T of the breast W and a thickness t of the member on the upper surface 34A side of the compression member 34 (the member on the surface in contact with the breast W). Accordingly, the synthesized two-dimensional image 80 including information in the depth direction is obtained. The synthesized two-dimensional image generation unit 51 causes the storage unit 62 to store the synthesized two-dimensional image 80 including the information in the depth direction.

On the other hand, the ultrasound image acquisition unit 52 has a function of acquiring an ultrasound image U. As an example, the ultrasound image U of the present embodiment shows a plurality of first cross-sectional ultrasound images 90 shown in FIG. 6. The ultrasound image acquisition unit 52 acquires an ultrasound image U of the breast of the specific subject designated by the image display instruction described above from the image storage system 19 via the I/F unit 64. The ultrasound image acquisition unit 52 outputs the acquired ultrasound images U to the image generation unit 53.

The image generation unit 53 generates a plurality of ultrasound images of the breast W, which are cross-sectional images in a direction intersecting the ultrasound image U, by reconstructing the plurality of ultrasound images U. As described above, in the present embodiment, since the ultrasound image U is a first cross-sectional ultrasound image 90 that is a cross-sectional image of the breast W in the left-right direction, the image generation unit 53 generates a plurality of second cross-sectional ultrasound images that are cross-sectional images of the breast W in the front-rear direction. That is, the image generation unit 53 synthesizes the ultrasound images 90 to generate a plurality of second cross-sectional ultrasound images that are cross-sectional images in a direction intersecting the imaging table 40 and the first cross-sectional ultrasound image 90.

In addition, the image generation unit 53 generates at least one of a cross-sectional image (hereinafter referred to as a third cross-sectional ultrasound image) of a plane that can be considered parallel to the imaging surface 40A of the imaging table 40 or a three-dimensional ultrasound image of the breast W by reconstructing the plurality of ultrasound images U, that is, the plurality of first cross-sectional ultrasound images 90. Hereinafter, for simplification of description, a case in which the image generation unit 53 generates a three-dimensional ultrasound image will be described.

Note that the method by which the image generation unit 53 generates a plurality of second cross-sectional ultrasound images and a three-dimensional ultrasound image from the plurality of ultrasound images U (the plurality of first cross-sectional ultrasound images 90) is not particularly limited, and any known method can be used. The image generation unit 53 causes the storage unit 62 to store the plurality of generated second cross-sectional ultrasound images and the generated three-dimensional ultrasound image.

The position information acquisition unit 54 has a function of acquiring position information S indicating a position in the synthesized two-dimensional image generated by the synthesized two-dimensional image generation unit 51. The position information S is, for example, information indicating a designated position in a case in which the user designates a position on the synthesized two-dimensional image displayed on the display unit 68 through the operation unit 66, and specifically, is the XY coordinates of the designated position. Further, for example, in a case in which the user uses the operation unit 66 to move a movable cross section line to designate the position of the cross section of the ultrasound image disposed on the synthesized two-dimensional image, which will be described in detail later, the position information S is information indicating the position of the moved cross section line, and specifically, is the XY coordinates of the position of the cross section line. The position information acquisition unit 54 acquires the acquired position information S to the depth specifying unit 55.

The depth specifying unit 55 specifies the depth corresponding to the position represented by the position information S in the synthesized two-dimensional image. Specifically, the depth specifying unit 55 acquires the synthesized two-dimensional image from the storage unit 62 and specifies the depth D (see FIG. 6) based on the depth information of the pixel corresponding to the position represented by the position information S. The depth specifying unit 55 outputs the specified depth D to the display controller 56.

The display controller 56 has a function of causing an ultrasound image for display to be displayed on the display unit 68 to be displayed with information indicating the depth D specified by the depth specifying unit 55 added thereto. The display controller 56 of the present embodiment includes a display image selection unit 57 and a depth information addition unit 58, and the display image selection unit 57 and the depth information addition unit 58 cause the display unit 68 to display an ultrasound image for display to which depth information indicating the depth D is added.

Specifically, in a case in which at least one of the first cross-sectional ultrasound image 90 or the second cross-sectional ultrasound image is used as the ultrasound image for display, the display image selection unit 57 selects at least one of the first cross-sectional ultrasound image 90 or the second cross-sectional ultrasound image, which are cross-sectional images at a desired position, from the storage unit 62. The depth information addition unit 58 adds, as depth information, a line serving as an indicator (see lines LA to LC in FIG. 12 and the like) to a position corresponding to the depth D in at least one of the selected first cross-sectional ultrasound image 90 or second cross-sectional ultrasound image. On the other hand, in a case in which the three-dimensional ultrasound image is used as the ultrasound image for display, the display image selection unit 57 selects a three-dimensional ultrasound image according to the depth D from the storage unit 62, and sets the three-dimensional ultrasound image as an ultrasound image for display to which depth information is added. The display controller 56 causes the display unit 68 to display the ultrasound image for display to which the depth information is added in this manner.

Figure 7:
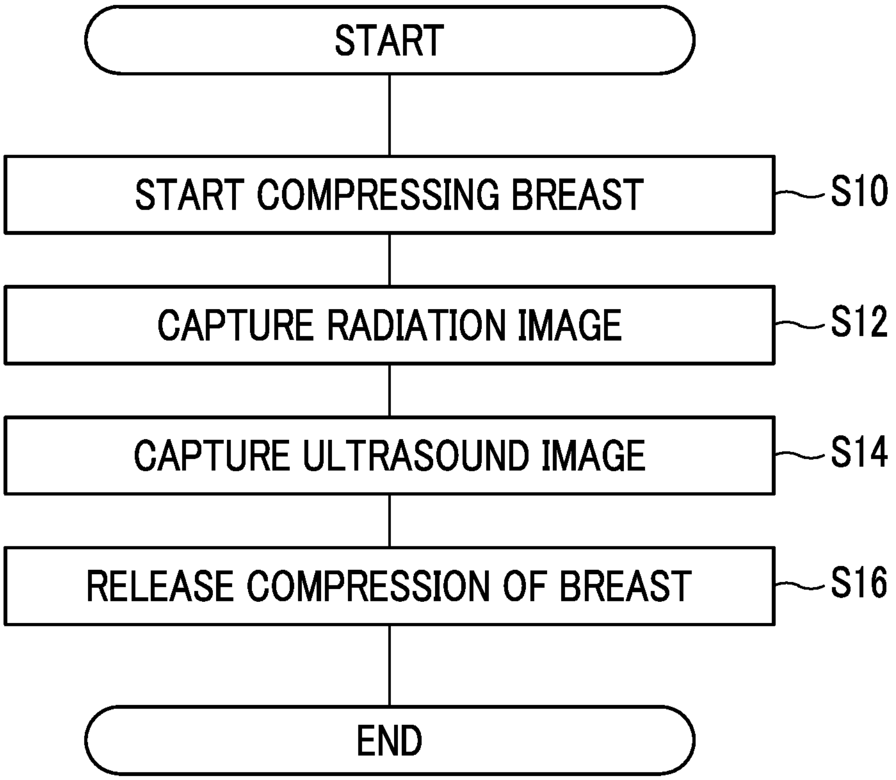
FIG. 7 is a flowchart showing an example of a flow of capturing a radiation image and an ultrasound image using the image capturing system according to the first embodiment.

Next, the operation of the image processing apparatus 18 according to the present embodiment will be described with reference to the drawings. First, the flow of capturing the radiation image X and the ultrasound image U using the image capturing system 1 will be described. FIG. 7 is a flowchart showing an example of a flow of capturing the radiation image X and the ultrasound image U using the image capturing system 1 according to the present embodiment.

First, the user positions the breast W of the examinee as a subject on the imaging surface 40A of the imaging table 40. In a case in which the positioning is completed, the user inputs an instruction to compress the breast W using the operation unit 26. Therefore, in Step S10 of FIG. 7, the controller 20 of the mammography apparatus 10 starts compressing the breast W using the compression member 34. Specifically, in a case in which an instruction to compress the breast W is received, the controller 20 moves the compression member 34 in the compression direction, and puts the breast W into a compression state between the compression member 34 and the imaging surface 40A of the imaging table 40.

In the next Step S12, the mammography apparatus 10 captures the radiation image X of the breast W. Specifically, the user operates an irradiation switch included in the operation unit 26 to irradiate the breast W with the radiation R emitted from the radiation source 36R and to capture the radiation image X with the radiation detector 30. In the present embodiment, as described above, the tomosynthesis imaging is performed, and a plurality of projection images are acquired as the radiation image X. The radiation image X obtained by the mammography apparatus 10 is output to the console 12, is output from the console 12 to the image storage system 19 at a predetermined timing, and is stored in the image storage system 19.

In the next Step S14, the user scans the ultrasound probe 16A of the ultrasonography apparatus 16 to capture a plurality of ultrasound images U of the breast W in a compression state by the compression member 34. Specifically, after capturing the radiation image X, the user applies an acoustic matching member (not shown), such as echo jelly, onto the upper surface 34A of the compression member 34. Further, the user operates the ultrasound probe 16A to scan the upper surface 34A of the compression member 34 covered by the acoustic matching member with ultrasound, thereby capturing a plurality of ultrasound images U. In the present embodiment, as described above, a plurality of first cross-sectional ultrasound images 90 are acquired as ultrasound images U. The ultrasound image U obtained by the ultrasonography apparatus 16 is output from the ultrasonography apparatus 16 to the image storage system 19 at a predetermined timing and is stored in the image storage system 19.

In a case in which the capturing of the ultrasound image U ends, in the next Step S16, the compression of the breast W using the compression member 34 is released. Specifically, the user gives an instruction to release compression using the operation unit 26. In a case in which the release of the compression of the breast W is received, the controller 20 moves the compression member 34 in the decompression direction, moves the compression member 34 in a direction away from the imaging surface 40A of the imaging table 40, and releases the compression of the breast W using the compression member 34. In this way, in a case in which the process of Step S16 ends, the continuous imaging of the radiation image X and the ultrasound image U ends. In the present embodiment, as in the flow shown in FIG. 7, continuously capturing the radiation image X and the ultrasound image U while the breast W is kept in a compression state by the compression member 34 may be referred to as "continuous imaging". The order of capturing the radiation image X (Step S12 in FIG. 7) and capturing the ultrasound image U (Step S14 in FIG. 7) is not limited. However, from the viewpoint of reducing the compression time of the breast W, it is preferable to perform the capturing of the radiation image X first as in the present embodiment. In addition, the compression force with which the breast W is compressed by the compression member 34 may be weakened as long as it can be considered that there is no change in the compression state of the breast W between the capturing of the radiation image X and the capturing of the ultrasound image U. For example, the compression force by the compression member 34 may be weakened as long as that it can be considered that no change has occurred in the degree of expansion of the mammary glands of the breast W.

Figure 8:
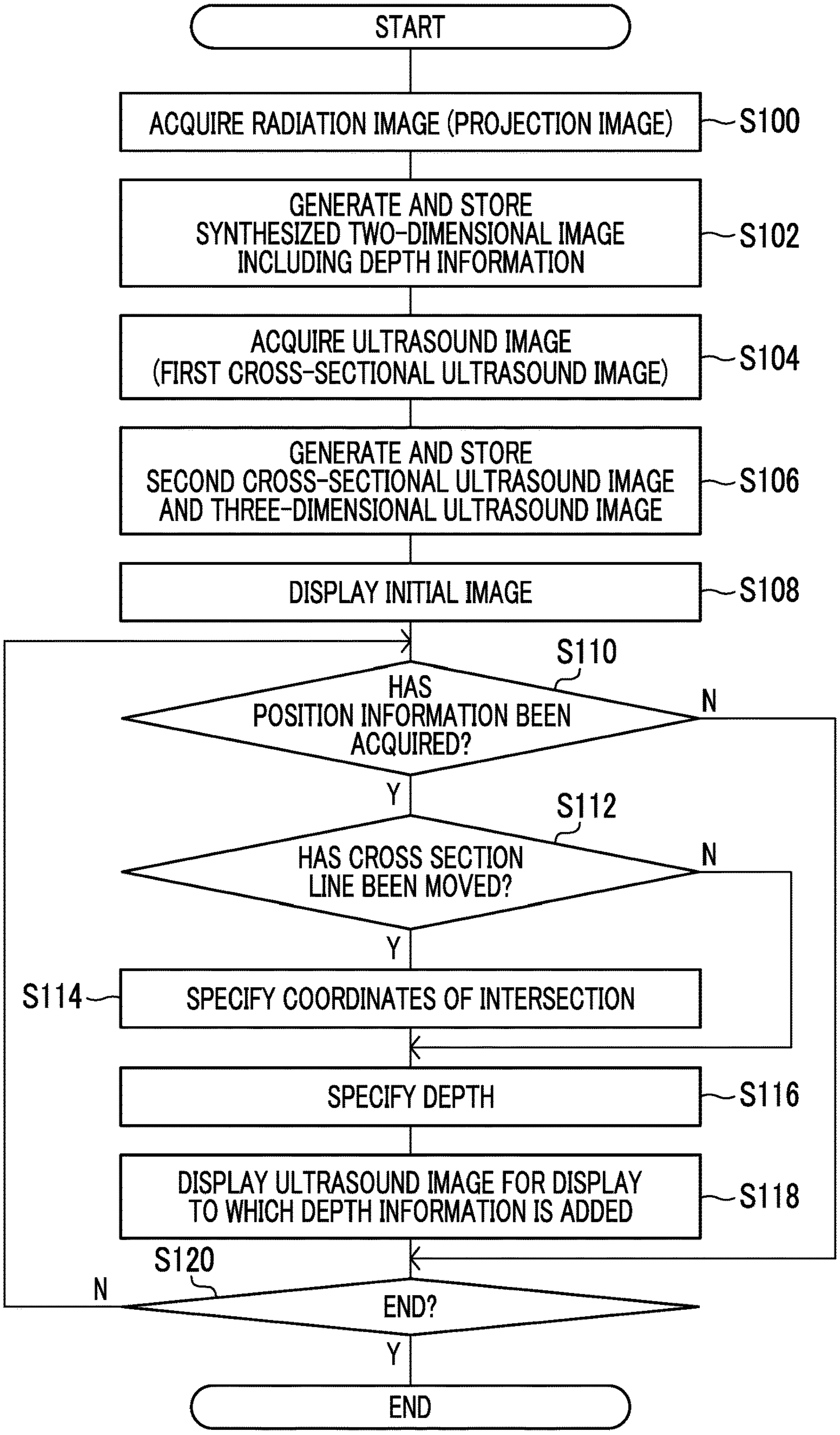
FIG. 8 is a flowchart showing an example of a flow of image processing in the image processing apparatus according to the first embodiment.

In a case in which the continuous imaging of the radiation image X and the ultrasound image U ends in this way, the image processing by the image processing apparatus 18 is performed. As an example, as described above, in a case in which the image processing apparatus 18 according to the present embodiment receives an image display instruction input by the user, the CPU 60A of the controller 60 executes the image processing program 61 stored in the ROM 60B to execute image processing, an example of which is shown in FIG. 8. FIG. 8 is a flowchart showing an example of a flow of image processing in the image processing apparatus 18 according to the present embodiment.

First, in Step S100, the radiation image acquisition unit 50 acquires the radiation image X, which is a series of projection images obtained by tomosynthesis imaging of the breast W of the examinee, from the image storage system 19, as described above.

In the next Step S102, the synthesized two-dimensional image generation unit 51 generates the synthesized two-dimensional image 80 including the depth information from the radiation image X which is an example of the projection image and causes the storage unit 62 to store the synthesized two-dimensional image 80, as described above.

In the next Step S104, the ultrasound image acquisition unit 52 acquires the ultrasound images U, which are a plurality of first cross-sectional ultrasound images 90, from the image storage system 19, as described above.

In the next Step S106, the image generation unit 53 generates a plurality of second cross-sectional ultrasound images and a three-dimensional ultrasound image from the plurality of first cross-sectional ultrasound images 90 and causes the storage unit 62 to store the plurality of generated second cross-sectional ultrasound images and the generated three-dimensional ultrasound image, as described above.

Figure 9:
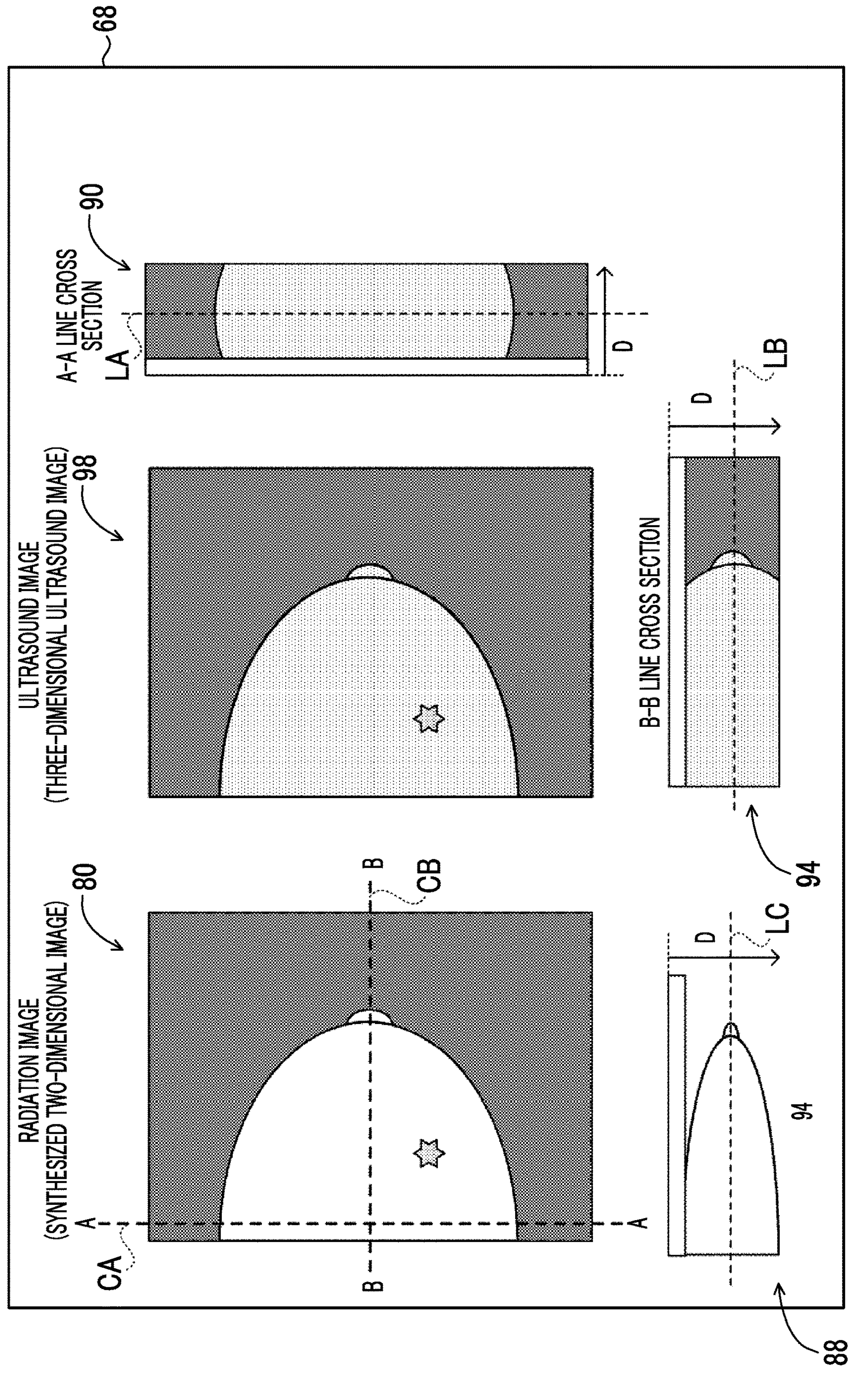
FIG. 9 is a diagram showing a display example of an ultrasound image for display to which depth information is added and a synthesized two-dimensional image.

In the next Step S108, the display controller 56 causes the display unit 68 to display initial images of the synthesized two-dimensional image 80, the first cross-sectional ultrasound image 90, a second cross-sectional ultrasound image 94, and a three-dimensional ultrasound image 98, an example of which is shown in FIG. 9. As shown in FIG. 9, in the present embodiment, the initial image of the first cross-sectional ultrasound image 90 is a cross-sectional view at a position on the chest wall side, and the initial image of the second cross-sectional ultrasound image 94 is a cross-sectional view at the center position of the breast in the left-right direction (up-down direction in FIG. 9). Therefore, as shown in FIG. 9, the initial image of the synthesized two-dimensional image 80 is a synthesized two-dimensional image 80 in which a cross section line CA representing the cross section shown by the first cross-sectional ultrasound image 90 is disposed on the chest wall side, which is the initial position, and a cross section line CB representing the cross section shown by the second cross-sectional ultrasound image 94 is disposed at the center position of the left and right sides of the breast W.

In addition, the display controller 56 causes the display unit 68 to display the first cross-sectional ultrasound image 90 designated by the cross section line CA on the synthesized two-dimensional image 80 and the second cross-sectional ultrasound image 94 designated by the cross section line CB on the synthesized two-dimensional image 80 as initial images related to the ultrasound image.

Further, as shown in FIG. 9, in the present embodiment, the initial position of the depth D is set at the center position of the maximum depth (the sum of the thickness T of the breast and the thickness of the compression member 34). Therefore, the display controller 56 causes the display unit 68 to display the three-dimensional ultrasound image 98 at the depth D indicating the center position. Further, the display controller 56 displays lines LA and LB serving as indicators at positions corresponding to the depths D on the first cross-sectional ultrasound image 90 and the second cross-sectional ultrasound image 94, as depth information.

In the present embodiment, in a case in which the synthesized two-dimensional image 80, the first cross-sectional ultrasound image 90, and the like are displayed on the display unit 68, as shown in FIG. 9, a schematic diagram 88 of the breast W to which a line LC serving as an indicator indicating the position in the depth direction is added is also displayed. In this way, by displaying the schematic diagram 88 to which the line LC is added, it is possible to present the position of the displayed first cross-sectional ultrasound image 90 in the depth direction to the user in an easy-to-understand manner.

In the next Step S110, the position information acquisition unit 54 determines whether or not the position information S has been acquired. In a case in which the user designates a position on the displayed synthesized two-dimensional image 80 using the operation unit 66, or in a case in which at least one of the cross section line CA or the cross section line CB on the synthesized two-dimensional image 80 is moved using the operation unit 66, the position information acquisition unit 54 acquires the position information S. As described above, in a case in which the user designates a position on the displayed synthesized two-dimensional image 80 using the operation unit 66, coordinates of the designated position become the position information S. In a case in which the user moves at least one position of the cross section line CA or the cross section line CB on the synthesized two-dimensional image 80 using the operation unit 66, information indicating the positions of the cross section line CA and the cross section line CB becomes the position information S.

In a case in which the position information acquisition unit 54 has not acquired the position information S, the determination in Step S110 is negative, and the process proceeds to Step S120. On the other hand, in a case in which the position information acquisition unit 54 has acquired the position information S, the determination in Step S110 is affirmative, and the process proceeds to Step S112.

In Step S112, the depth specifying unit 55 determines whether or not the acquired position information S is information indicating that at least one of the cross section line CA or the cross section line CB has been moved. In a case in which the position information S is the coordinates of the designated position, the determination in Step S112 is negative, and the process proceeds to Step S116. On the other hand, in a case in which the position information S is the information indicating the positions of the cross section line CA and the cross section line CB, the determination in Step S112 is affirmative, and the process proceeds to Step S114.

In Step S114, the depth specifying unit 55 specifies the position (XY coordinates) of the intersection of the cross section lines CA and CB from the information indicating the positions of the cross section lines CA and CB, which is the position information S.

In the next Step S116, the depth specifying unit 55 specifies the depth corresponding to the position represented by the position information S in the synthesized two-dimensional image 80, as described above. Specifically, the depth D is specified based on the depth information of the pixel corresponding to the coordinates of the position designated by the user or the coordinates of the intersection of the cross section line CA and the cross section line CB in the synthesized two-dimensional image 80.

Figure 10:
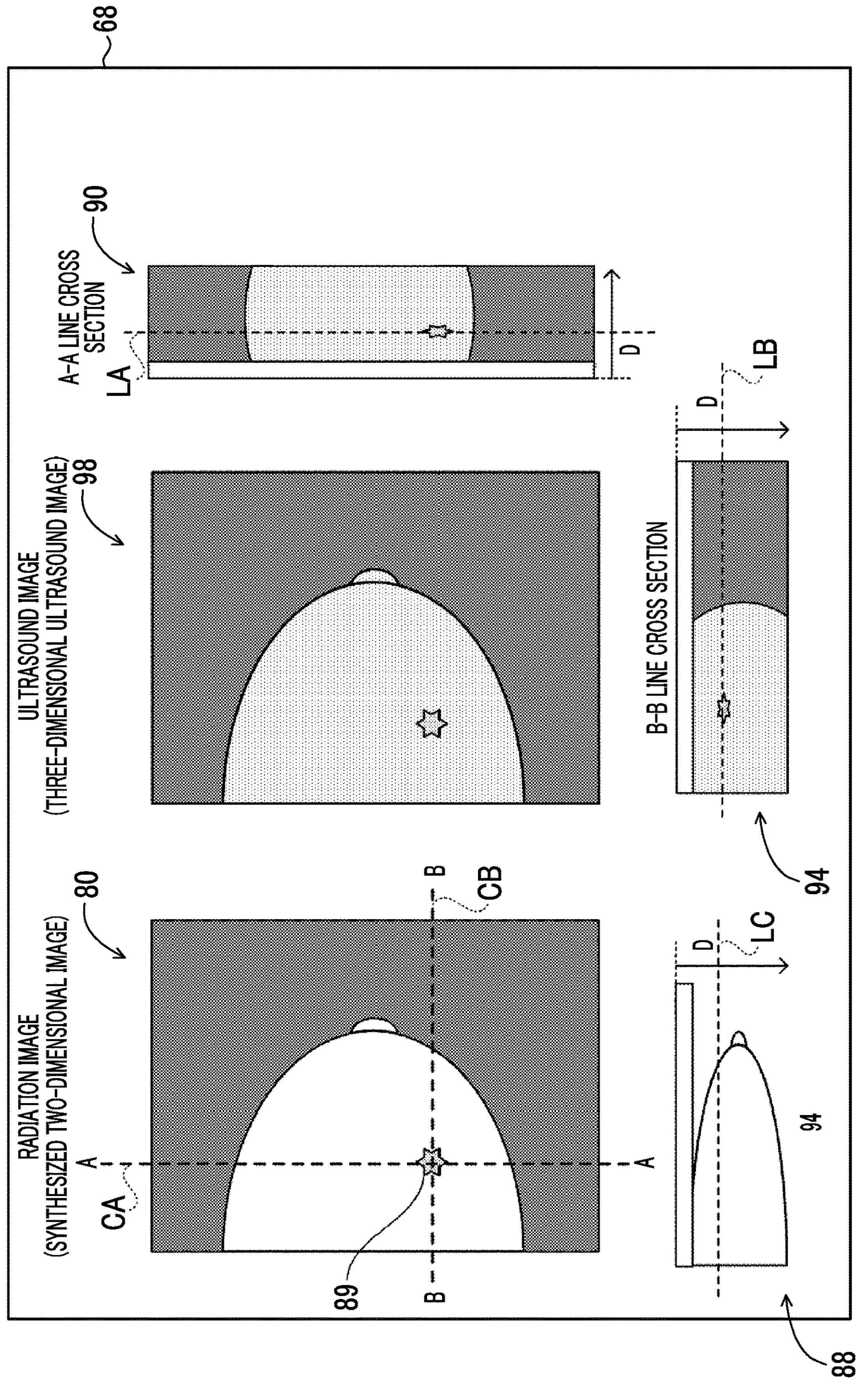
FIG. 10 is a diagram showing a display example of an ultrasound image for display to which depth information is added and a synthesized two-dimensional image.

In the next Step S118, the display controller 56 causes the display unit 68 to display the ultrasound image for display to which the depth information is added, as described above. FIG. 10 shows an example of the display state on the display unit 68. FIG. 10 shows a display example in a case in which the user designates a tumor 89 included in the synthesized two-dimensional image 80 using the operation unit 66, or in a case in which the user moves the cross section line CA and the cross section line CB using the operation unit 66 in accordance with the position of the tumor 89. Note that in a case in which the user designates a position on the synthesized two-dimensional image 80 using the operation unit 66, the display controller 56 displays the cross section line CA and the cross section line CB at a position corresponding to the position designated by the user. In the example shown in FIG. 10, in the first cross-sectional ultrasound image 90, a line LA is provided at a position at the depth D at which the tumor 89 is present, and in the second cross-sectional ultrasound image 94, a line LB is provided at a position at the depth D at which the tumor 89 is present. Further, the first cross-sectional ultrasound image 90 is a three-dimensional ultrasound image according to the depth D at which the tumor 89 is present.

In the next Step S120, the display controller 56 determines whether or not to end the display. As an example, in the present embodiment, in a case in which the display is ended, the user inputs an instruction to end the display using the operation unit 66. Therefore, the display controller 56 makes a negative determination in Step S120 until an instruction to end the display is input, returns to Step S110, and repeats the processes of Steps S110 to S118. On the other hand, in a case in which an instruction to end the display is input, the determination in Step S120 becomes affirmative, and the image processing shown in FIG. 8 ends.

Second Embodiment

Another embodiment of the technology of the present disclosure will be described below.

In addition, in the present embodiment, the overall configuration of the image capturing system 1 and the configurations and operations of the mammography apparatus 10, the console 12, the ultrasonography apparatus 16, and the image storage system 19 are the same as those in the first embodiment. Therefore, the description thereof will be omitted.

On the other hand, in the present embodiment, since the functions and operations of the image processing apparatus 18 are different from those of the image processing apparatus 18 according to the first embodiment, the image processing apparatus 18 will be described in detail. Note that the hardware configuration of the image processing apparatus 18 is the same as that in the image processing apparatus 18 (see FIG. 3) according to the first embodiment. Therefore, the description of the hardware configuration will be omitted.

FIG. 11 is a functional block diagram showing an example of the functions of the image processing apparatus 18 according to the present embodiment. The image processing apparatus 18 according to the present embodiment is different from the image processing apparatus 18 according to the first embodiment (see FIG. 4) in that it further comprises a region-of-interest detection unit 59. As an example, in the image processing apparatus 18 according to the present embodiment, the CPU 60A of the controller 60 executes the image processing program 61, and thereby the CPU 60A functions as the radiation image acquisition unit 50, the synthesized two-dimensional image generation unit 51, the ultrasound image acquisition unit 52, the image generation unit 53, the position information acquisition unit 54, the depth specifying unit 55, the display controller 56, and the region-of-interest detection unit 59.

Figure 12:
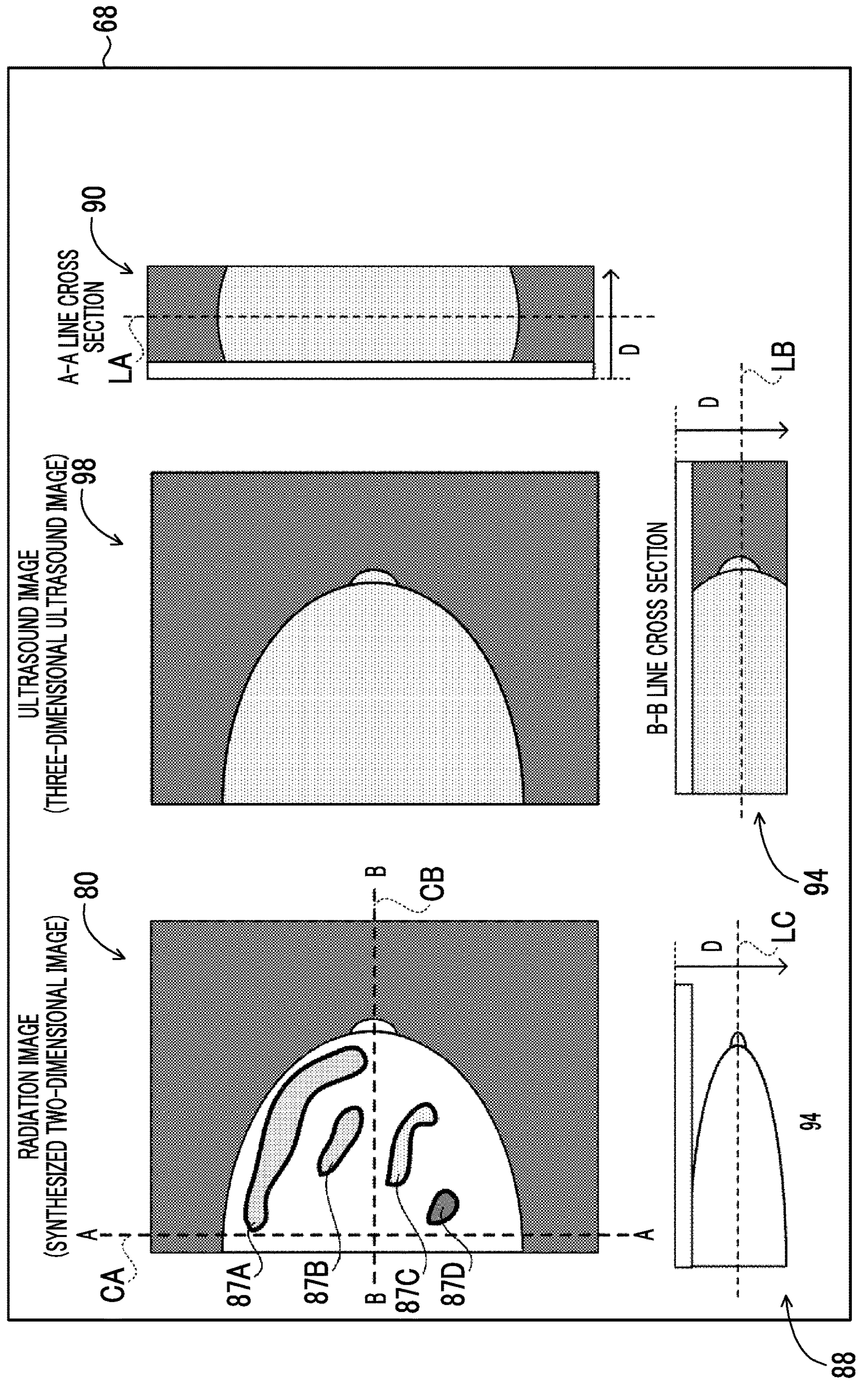
FIG. 12 is a diagram showing an example of a display of a synthesized two-dimensional image on which information indicating a region of interest is superimposed.

The region-of-interest detection unit 59 has a function of detecting a region of interest from the synthesized two-dimensional image 80. Note that the method by which the region-of-interest detection unit 59 detects the region of interest from the synthesized two-dimensional image 80 is not particularly limited. For example, the region of interest may be detected from the synthesized two-dimensional image 80 using existing mammography computer-aided detection (CAD). The region-of-interest detection unit 59 outputs information indicating the detected region of interest to the display controller 56. The display controller 56 of the present embodiment has a function of displaying information indicating the region of interest detected by the region-of-interest detection unit 59 on the synthesized two-dimensional image 80 in addition to the functions of the display controller 56 of the first embodiment. FIG. 12 shows an example of a display of the synthesized two-dimensional image 80 on which information indicating the region of interest is superimposed. In the example shown in FIG. 12, information indicating four regions of interest (regions of interest 87A to 87D) is displayed on the synthesized two-dimensional image 80. Note that the information indicating the region of interest is not particularly limited, and in the example shown in FIG. 12, a thick line indicating the outline of the detected region of interest is the information indicating the region of interest.

Figure 13:
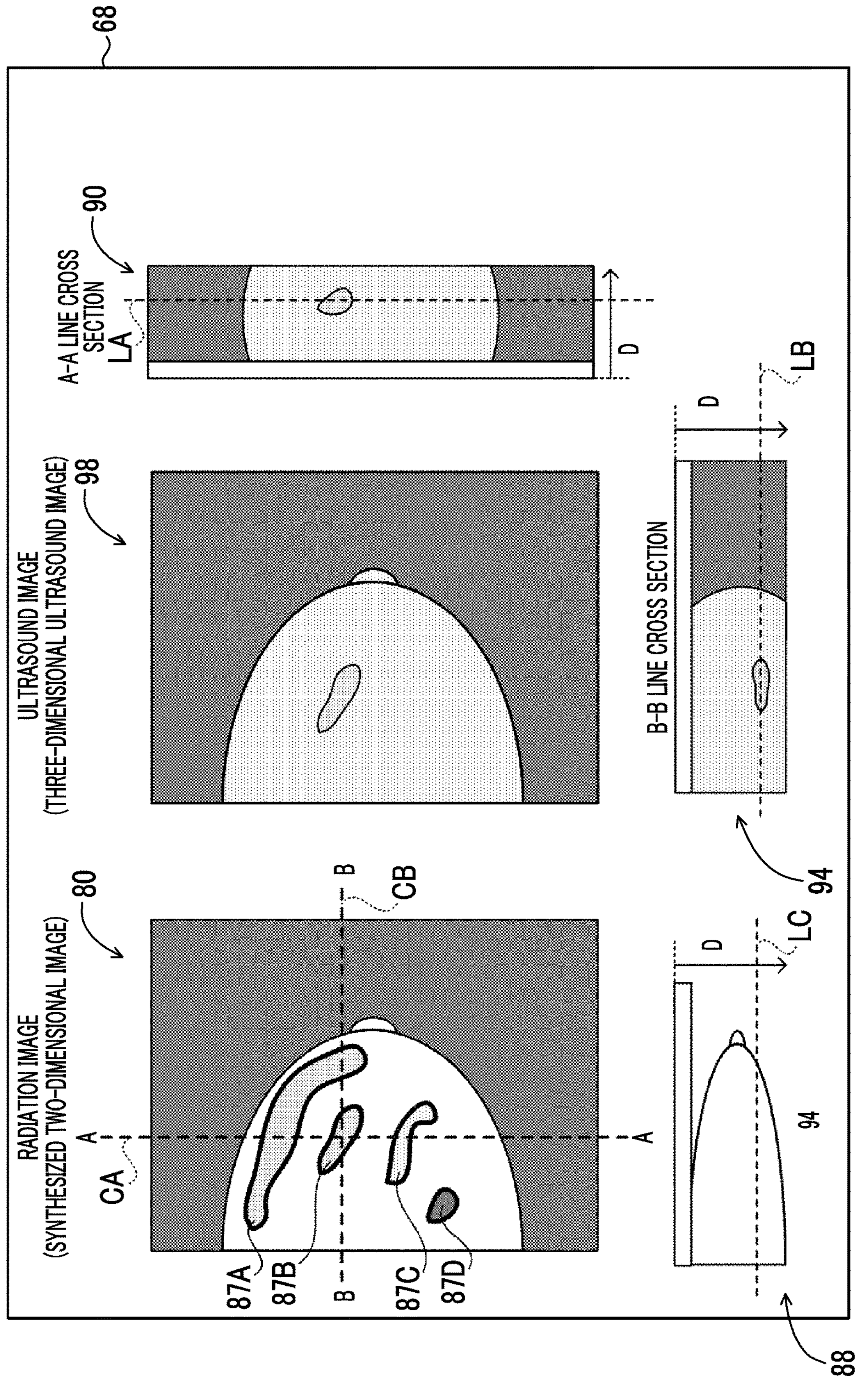
FIG. 13 is a diagram showing an example of a display in a state in which a region of interest is designated.

The user designates a region of interest among the regions of interest 87A to 87D that he or she wishes to check using an ultrasound image. For example, the user may designate the region of interest by moving the cross section line CA and the cross section line CB using the operation unit 66 such that the position of the intersection of the cross section line CA and the cross section line CB is within the region of interest that he or she wishes to designate. In addition, for example, the user may designate the region of interest by directly designating a position inside the region of interest that he or she wishes to designate using the operation unit 66. FIG. 13 shows a state in which the region of interest 87B is designated as an example. In this case, the position information S is information indicating the position of the region of interest (in the example of FIG. 13, the region of interest 87B) designated by the user.

The depth specifying unit 55 specifies the designated region of interest based on the position information S, and derives the centroid position or the maximum density position of the specified region of interest.

The depth specifying unit 55 specifies the depth D at which the designated region of interest is present based on the depth information of the pixel corresponding to the centroid position.

The display controller 56 displays ultrasound images for display (the first cross-sectional ultrasound image 90, the second cross-sectional ultrasound image 94, and the three-dimensional ultrasound image 98) to which depth information indicating the depth D specified by the depth specifying unit 55 is added in the same manner as the display controller 56 of the first embodiment. In a case in which the position on the synthesized two-dimensional image 80 designated by the user to designate the region of interest is different from the centroid position or maximum density position of the region of interest derived by the depth specifying unit 55, it is preferable that the display controller 56 moves the cross section line CA and the cross section line CB such that the centroid position or maximum density position of the region of interest derived by the depth specifying unit 55 intersects.

Figure 14:
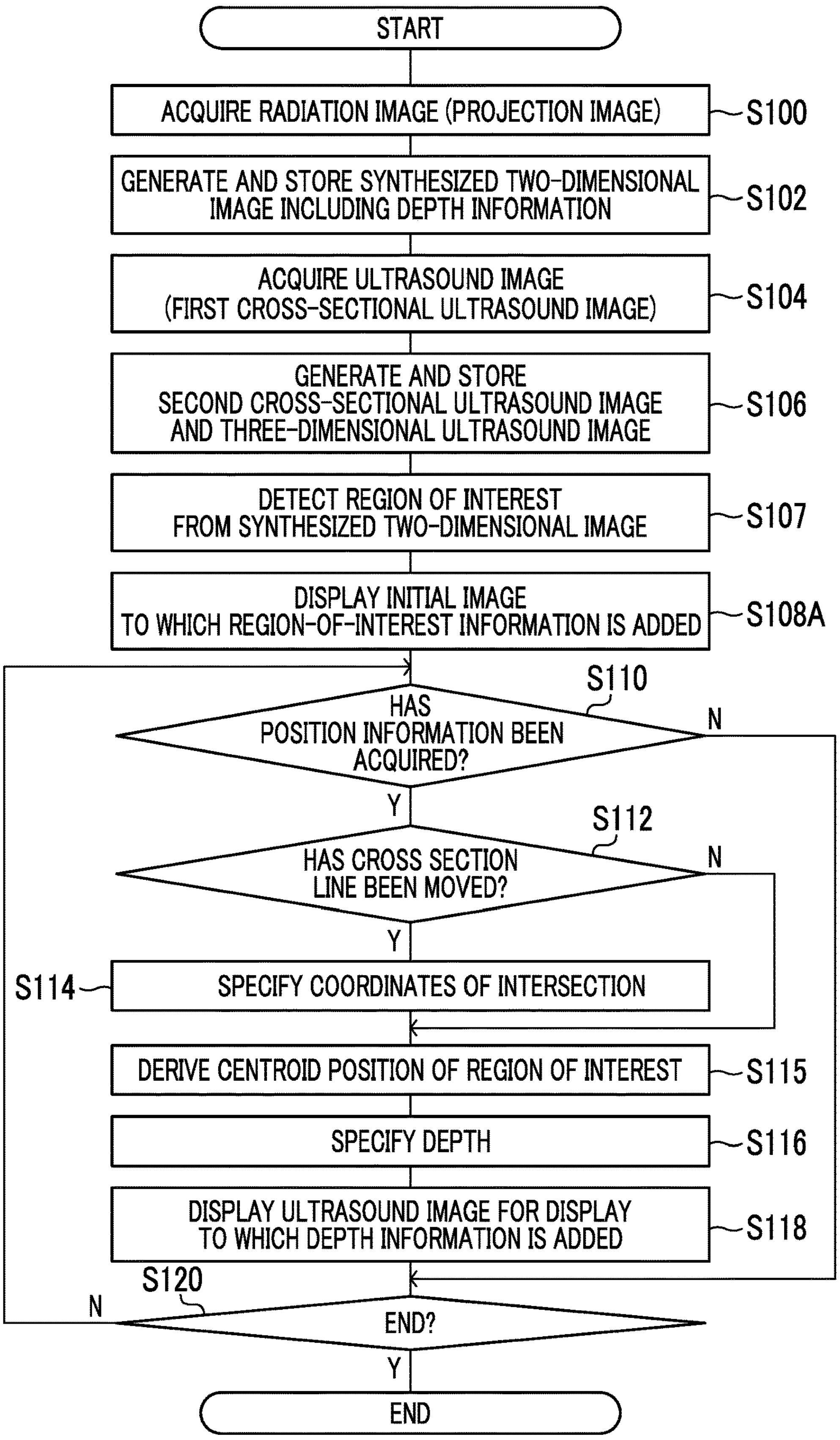
FIG. 14 is a flowchart showing an example of a flow of image processing in the image processing apparatus according to the second embodiment.

Next, the operation of the image processing apparatus 18 according to the present embodiment will be described. FIG. 14 is a flowchart showing an example of a flow of image processing in the image processing apparatus 18 according to the present embodiment. The image processing of the present embodiment shown in FIG. 14 is different from the image processing of the first embodiment (see FIG. 8) in that it includes the processes of Steps S107 and S108A instead of Step S108, and includes the process of Step S115 before Step S116.

In Step S107 of FIG. 14, the region-of-interest detection unit 59 detects a region of interest from the synthesized two-dimensional image 80, as described above.

In the next Step S108A, the display controller 56 causes the display unit 68 to display the initial image (see FIG. 12) in a state in which information indicating the region of interest detected in the above Step S107 is displayed on the synthesized two-dimensional image 80, as described above.

In a case in which the information indicating the region of interest (in FIG. 12, the information indicating the regions of interest 87A to 87D) is displayed on the synthesized two-dimensional image 80 in this way, as described above, the user designates the region of interest, and the position information acquisition unit 54 acquires the position information S indicating the position of the designated region of interest.

In Step S115, the depth specifying unit 55 derives the centroid position of the specified region of interest based on the position information S. Note that, as described above, the maximum density position of the region of interest may be derived instead of the centroid position. In the next Step S116, the depth specifying unit 55 specifies the depth D of the centroid position derived in the above Step S115, as described above.

Accordingly, in Step S118, as described above, the display controller 56 causes the display unit 68 to display the synthesized two-dimensional image 80, the first cross-sectional ultrasound image 90, the second cross-sectional ultrasound image 94, and the three-dimensional ultrasound image 98, as shown in FIG. 13.

In this way, with the image processing apparatus 18 according to the present embodiment, the first cross-sectional ultrasound image 90, the second cross-sectional ultrasound image 94, and the three-dimensional ultrasound image 98 are displayed according to the region of interest detected by the region-of-interest detection unit 59 from the synthesized two-dimensional image 80. Note that, in the present embodiment, the aspect in which the first cross-sectional ultrasound image 90, the second cross-sectional ultrasound image 94, and the three-dimensional ultrasound image 98 are displayed according to the region of interest designated by the user among the regions of interest detected by the region-of-interest detection unit 59 has been described. However, the present disclosure is not limited to the present aspect, and for example, the information indicating the region of interest may be obtained by automatically moving and displaying the cross section line CA and the cross section line CB such that the centroid position or maximum density position of the region of interest detected by the region-of-interest detection unit 59 intersects. In this case, even in a case in which the user does not designate the region of interest, the first cross-sectional ultrasound image 90, the second cross-sectional ultrasound image 94, and the three-dimensional ultrasound image 98 are displayed in a state according to the depth based on the depth information of the pixel corresponding to the intersection of the cross section line CA and the cross section line CB.

Modification Example 1

Figure 15:
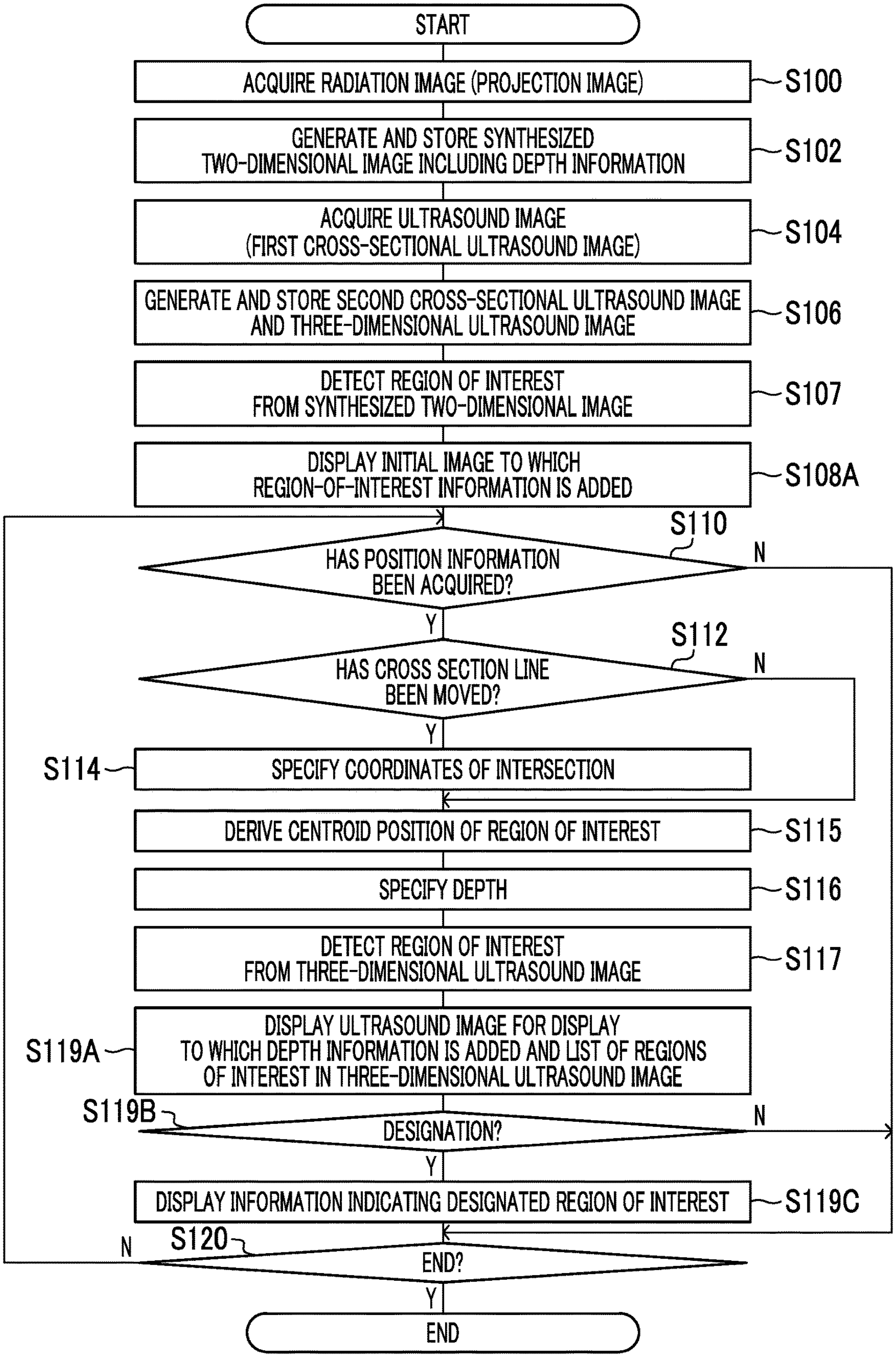
FIG. 15 is a flowchart showing an example of a flow of image processing in an image processing apparatus according to Modification Example 1.

Note that in the above description, the region of interest was detected from the synthesized two-dimensional image 80, but the region of interest may also be configured to be detected from the ultrasound image. The operation of the image processing apparatus 18 in this case will be described as a modification example. FIG. 15 is a flowchart showing an example of a flow of image processing in the present modification example. The image processing of the present modification example shown in FIG. 15 is different from the image processing of the above embodiment (see FIG. 14) in that it includes the processes of Step S117 and Steps S119A to S119C instead of Step S118.

In the image processing of the present modification example, after specifying the depth D of the region of interest based on the centroid position of the region of interest in the synthesized two-dimensional image 80, the region-of-interest detection unit 59 detects the region of interest from the three-dimensional ultrasound image 98 in Step S117. Note that the region of interest detected from the synthesized two-dimensional image 80 is an example of a first region of interest of the present disclosure, and the region of interest detected from the ultrasound image is an example of a second region of interest of the present disclosure.

Figure 16:
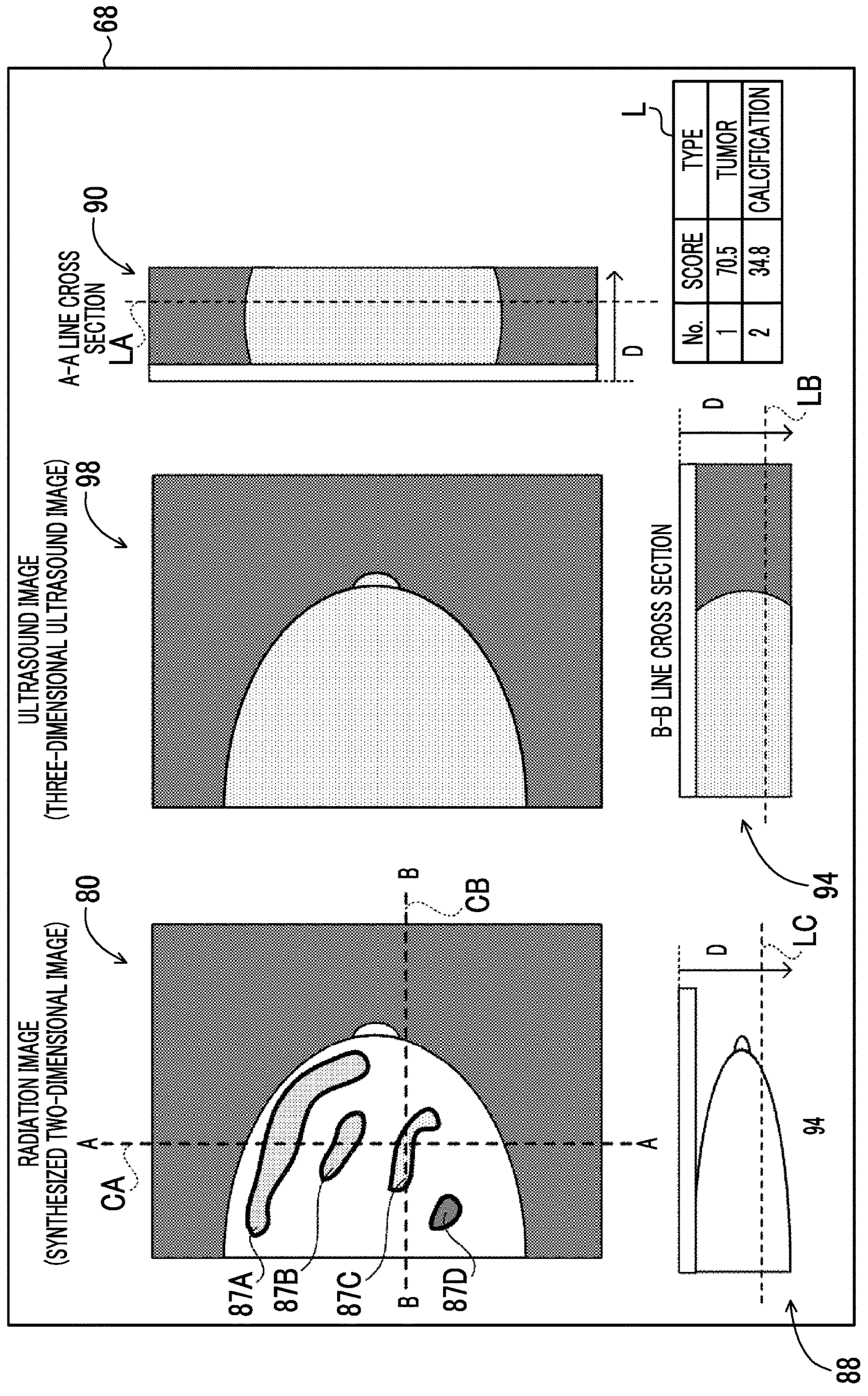
FIG. 16 is a diagram showing an example of a display state in Modification Example 1.

In the next Step S119A, as shown in FIG. 16, the display controller 56 causes the display unit 68 to display an ultrasound image for display to which depth information is added and to also display a list L of regions of interest in the three-dimensional ultrasound image 98 detected in the above Step S117, in the same manner as described above. The list L is a list of scores (certainty) for each of a plurality of regions of interest detected in the three-dimensional ultrasound image 98. For example, in a case in which the region-of-interest detection unit 59 detects the region of interest from the three-dimensional ultrasound image 98 using the mammography CAD as described above, a score is given according to a result of the CAD, and the higher the score, the higher the likelihood of a lesion in the region of interest. From the displayed list L, the user uses the operation unit 66 to designate a region of interest that he or she wishes to check.

In the next Step S119B, the display controller 56 determines whether or not the list L has been designated. In a case in which the list L has not been designated, the determination in Step S119B is negative, and the process proceeds to Step S120. On the other hand, in a case in which the list L has been designated, the determination in Step S119B is affirmative, and the process proceeds to Step S119C.

Figure 17:
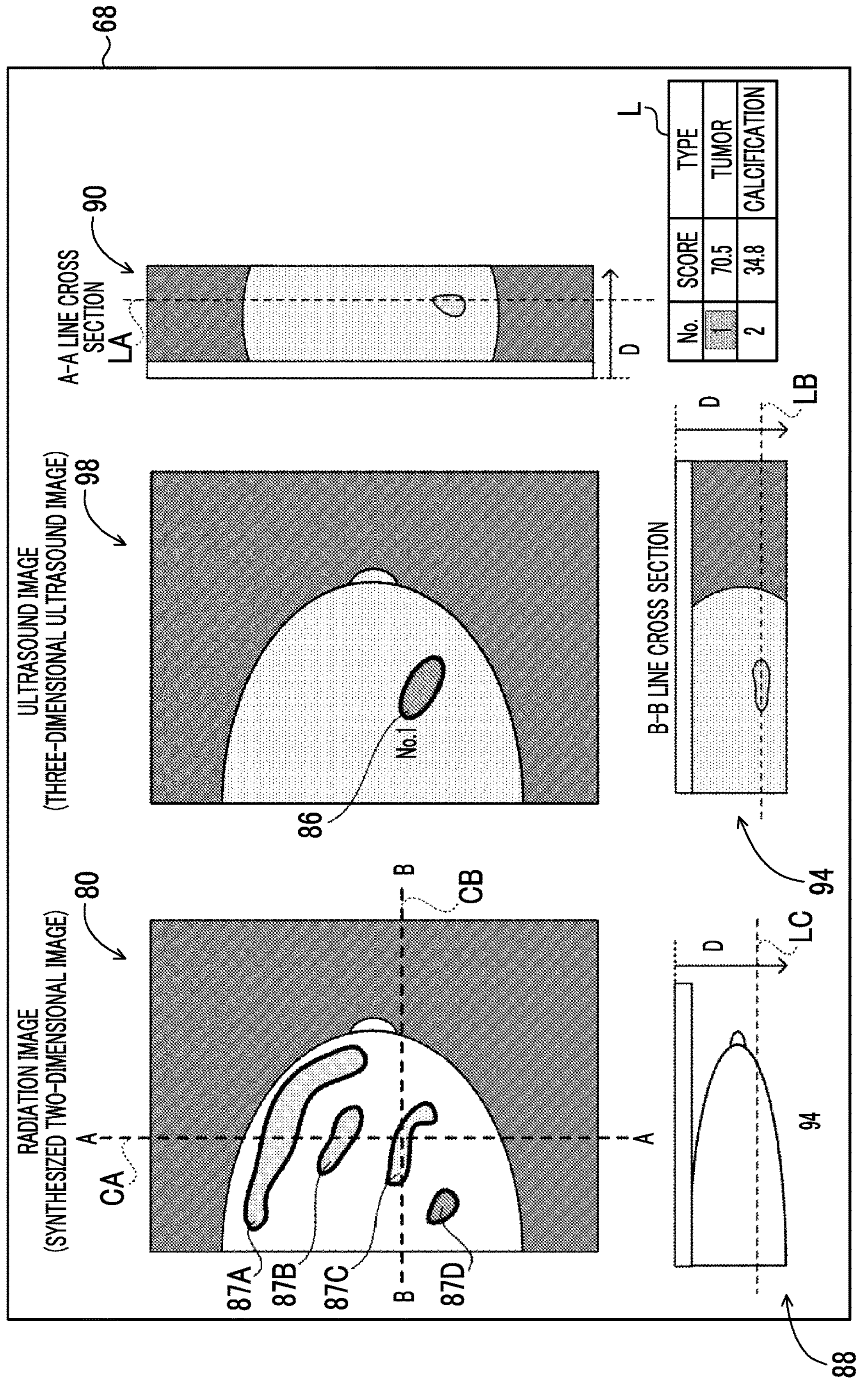
FIG. 17 is a diagram showing an example of a display state in Modification Example 1.

In Step S119C, the display controller 56 displays, on the three-dimensional ultrasound image 98 displayed on the display unit 68, the information indicating the region of interest designated in the list L by the user. FIG. 17 shows an example of a state in which "No. 1" is selected from the list L. On the three-dimensional ultrasound image 98 shown in FIG. 17, the outline of the region of interest 86 corresponding to "No. 1" of the list L is highlighted, and the number (No. 1) of the list L is displayed as region-of-interest information. Note that also for the first cross-sectional ultrasound image 90 and the second cross-sectional ultrasound image 94 displayed on the display unit 68, in a case in which the cross section includes the region of interest designated in the list L (region of interest 86 in FIG. 17), it is preferable that information indicating the region of interest is also displayed on the displayed first cross-sectional ultrasound image 90 and second cross-sectional ultrasound image 94.

In a case in which a region of interest is detected from an ultrasound image, such as the three-dimensional ultrasound image 98, by detecting the region of interest in the ultrasound image corresponding to the vicinity of the region of interest detected from the synthesized two-dimensional image 80, and not detecting the region of interest in the region outside the vicinity, the accuracy of detecting the region of interest can be maintained while reducing the processing load required to detect the region of interest. Note that "vicinity of the region of interest" is not limited to a specific range from the region of interest, and may be optional. In addition, the range defined as "vicinity" may vary depending on the type of the object of interest (calcification, tumor, or the like).

Modification Example 2

Instead of the synthesized two-dimensional image 80, the region of interest may be detected from a tomographic image generated from the radiation image X. In this case, the region of interest detected from the tomographic image is an example of the region of interest of the technology of the present disclosure.

Figure 18:
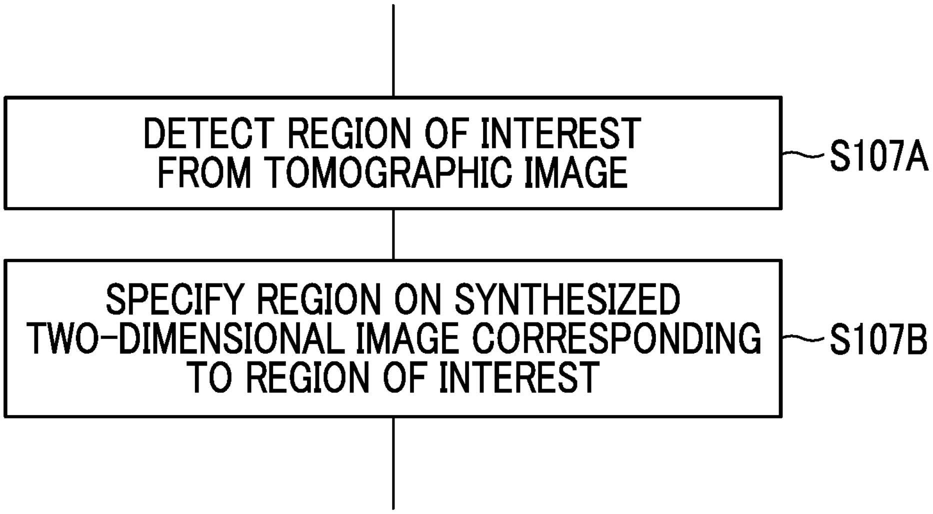
FIG. 18 is a flowchart showing a portion of a flow of image processing in an image processing apparatus according to Modification Example 2.

In the case of the present modification example, the process of Step S107 of the image processing shown in FIG. 14 or 15 only needs to be replaced with the processes of Steps S107A and S107B shown in FIG. 18. In the case of the present modification example, in a case in which the synthesized two-dimensional image generation unit 51 generates the synthesized two-dimensional image 80, the plurality of generated tomographic images are stored in the storage unit 62.

In Step S107A of FIG. 18, the region-of-interest detection unit 59 acquires a tomographic image from the storage unit 62 and detects a region of interest from the acquired tomographic image using CAD or the like.

In the next Step S107B, the region-of-interest detection unit 59 specifies a region (position) on the synthesized two-dimensional image 80 which corresponds to the region of interest detected from the tomographic image.

In this way, in the image processing apparatus 18 according to the present modification example, instead of directly detecting the region of interest from the synthesized two-dimensional image 80, the position of the region of interest on the synthesized two-dimensional image 80 is specified using a tomographic image. This makes it possible to easily detect a region of interest that is shadowed by other tissues and is difficult to detect.

As described above, with the image processing apparatus 18 according to each of the above embodiments and modification examples, it is possible to make it easier for the user to compare the synthesized two-dimensional image with the ultrasound image. Therefore, with the image processing apparatus 18 according to each of the above embodiments and modification examples, it is possible to easily recognize a three-dimensional structure of the breast tissue.

Note that as a premise for performing the image processing, it is preferable that the thickness of the breast in a compression state by the compression member 34 in the capturing of the radiation image X is the same as the thickness of the breast in a compression state by the compression member 34 in the capturing of the ultrasound image U. Therefore, it is preferable to perform the process of Step S90 shown in FIG. 19 before the first Step S100 of the image processing described above.

Figure 19:
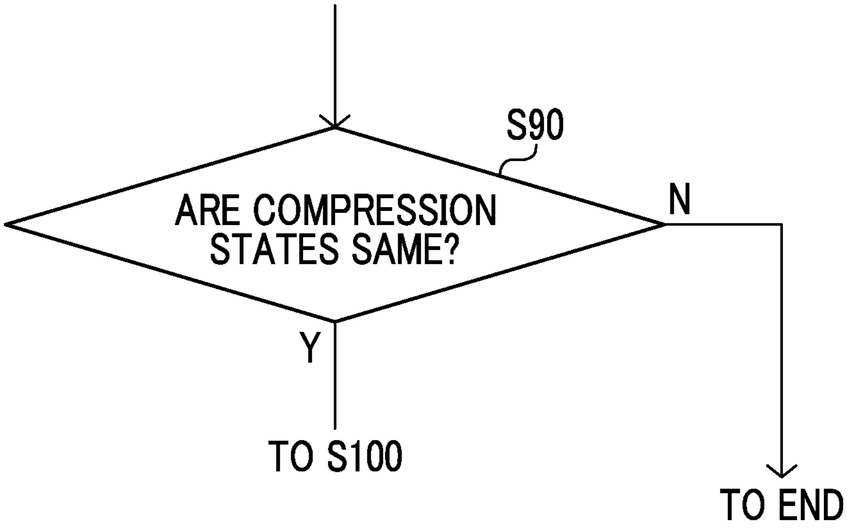
FIG. 19 is a flowchart for describing image processing in a case in which determination is made for a compression state of a breast.

In Step S90 of FIG. 19, the radiation image acquisition unit 50 determines whether or not the compression state of the breast W in the capturing of the radiation image X and the compression state of the breast W in the capturing of the ultrasound image U are the same. For example, as described above with reference to FIG. 7, in a case in which the capturing of the radiation image X and the capturing of the ultrasound image U are performed continuously without releasing the compression of the breast W, the compression states can be considered to be the same.

Further, for example, in a case in which at least one compression condition, such as the pressure of compressing the breast W by the compression member 34, the type of the compression member 34, or the distance between the compression member 34 and the imaging surface 40A of the imaging table 40, is the same, the compression states of the breast W can be considered to be the same. Moreover, for example, in a case in which the state of the breast, which is at least one of the thickness of the breast W in a compression state by the compression member 34, the contact area between the breast W in the compression state and the imaging surface 40A of the imaging table 40, or the contact area between the breast W in the compression state and the compression member 34, is the same, the compression states of the breast W can be considered to be the same.

Further, for example, in a case in which the state of the breast W itself, such as the hardness or size of the breast W, is different between the capturing of the radiation image X and the capturing of the ultrasound image U, the compression states of the breast W cannot be considered to be the same.

The radiation image acquisition unit 50 determines whether or not the compression states are the same based on these determination criteria. In a case in which the compression states are not the same, the negative determination is made in Step S90, and the image processing ends. On the other hand, in a case in which the compression states can be considered to be the same, the determination in Step S90 is affirmative and the process proceeds to Step S100 to execute the above-described image processing.

In Modification Example 1 described above, in addition to the first embodiment, the aspect has been described as adding a series of processes in which a region of interest is detected from an ultrasound image, a list L of regions of interest is displayed, and information indicating the region of interest selected from the list L is displayed on the ultrasound image. However, a series of processes related to the region of interest in the ultrasound image (hereinafter referred to as "region-of-interest-related processing") may be performed separately from the image processing described in the first embodiment. In this case, the following processing flow is performed as region-of-interest-related processing in the ultrasound image. First, a synthesized two-dimensional image of a radiation image of the breast W imaged in a compression state by the compression member 34 or a tomographic image reconstructed from the radiation image is acquired. Further, a first region of interest is detected from the synthesized two-dimensional image or the tomographic image. In addition, a plurality of ultrasound images of the breast imaged in a compression state by the compression member, the compression state which is considered to be the same as that in capturing a radiation image, are acquired. Further, a region-of-interest ultrasound image corresponding to the first region of interest is acquired from the plurality of ultrasound images, and a second region of interest is detected from the region-of-interest ultrasound image. Then, a synthesized two-dimensional image or a tomographic image to which information (first region-of-interest information) indicating the first region of interest is added and a region-of-interest ultrasound image to which information (second region-of-interest information) indicating the second region of interest is added are displayed. An apparatus that performs such region-of-interest-related processing may be the image processing apparatus 18, or may be an apparatus separate from the image processing apparatus 18. Further, depending on the desire of the user, only the region-of-interest-related processing may be performed as appropriate.

Figure 20:
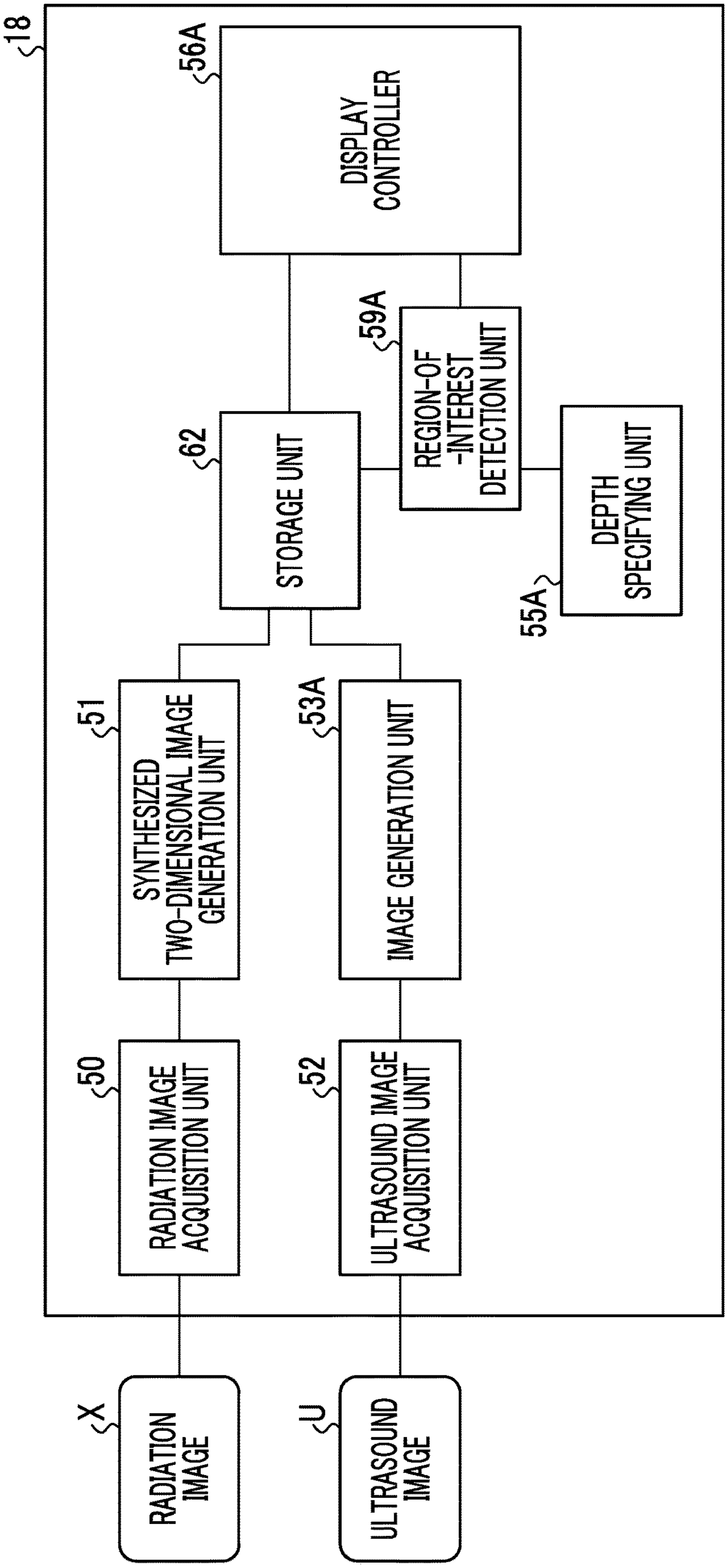
FIG. 20 is a functional block diagram showing an example of a function of the image processing apparatus related to execution of region-of-interest-related processing.

As a specific example, a case in which the image processing apparatus 18 performs such region-of-interest-related processing will be described with reference to FIG. 20. FIG. 20 is a functional block diagram showing an example of a function of the image processing apparatus 18 related to execution of region-of-interest-related processing. The image processing apparatus 18 shown in FIG. 20 comprises the radiation image acquisition unit 50, the synthesized two-dimensional image generation unit 51, the ultrasound image acquisition unit 52, the image generation unit 53, a depth specifying unit 55A, a display controller 56A, and a region-of-interest detection unit 59A.

The radiation image acquisition unit 50, the synthesized two-dimensional image generation unit 51, and the ultrasound image acquisition unit 52 have the same functions as those in the above-described first embodiment, and therefore the description thereof will be omitted.

On the other hand, the image generation unit 53A of the present embodiment is similar to the image generation unit 53 of the above embodiment in that the image generation unit 53A generates a plurality of second cross-sectional ultrasound images of the breast W, which are cross-sectional images of the breast W in the front-rear direction by reconstructing the plurality of ultrasound images U (first cross-sectional ultrasound images 90), but is different from the image generation unit 53 of the above embodiment in that the image generation unit 53A does not generate a three-dimensional ultrasound image.

In addition, the region-of-interest detection unit 59A has a function of detecting a region of interest (first region of interest) from the synthesized two-dimensional image 80, and a function of detecting a region of interest (second region of interest) from each of the first cross-sectional ultrasound image 90 and the second cross-sectional ultrasound image. The method by which the region-of-interest detection unit 59A detects the first region of interest from the synthesized two-dimensional image 80 is the same as that of the region-of-interest detection unit 59 of the above embodiment. After detecting the first region of interest from the synthesized two-dimensional image 80, the region-of-interest detection unit 59A detects a second region of interest from each of the first cross-sectional ultrasound image 90 and the second cross-sectional ultrasound image. As an example, in the present specific example, the depth specifying unit 55A first specifies the depth of the first region of interest in the synthesized two-dimensional image 80, and outputs the specified depth of the first region of interest to the region-of-interest detection unit 59A. The region-of-interest detection unit 59A acquires the first cross-sectional ultrasound image 90 and the second cross-sectional ultrasound image, which are estimated to include the first region of interest, from the storage unit 62 based on the position (XY coordinates) of the first region of interest in the synthesized two-dimensional image 80. Further, the region-of-interest detection unit 59A extracts a region of the vicinity of the first region of interest from each of the first cross-sectional ultrasound image 90 and the second cross-sectional ultrasound image as a region-of-interest ultrasound image based on the depth and position of the first region of interest. In a case in which the region-of-interest ultrasound image is acquired from each of the first cross-sectional ultrasound image 90 and the second cross-sectional ultrasound image as described above, the region-of-interest detection unit 59A detects a region of interest (second region of interest) from the region-of-interest ultrasound image.

The region-of-interest detection unit 59A outputs the synthesized two-dimensional image 80 in association with information (first region-of-interest information) indicating the first region of interest to the display controller 56A. Further, the region-of-interest detection unit 59A outputs the region-of-interest ultrasound image in association with information (second region-of-interest information) indicating the second region of interest to the display controller 56A.

The display controller 56A causes the display unit 68 to display a synthesized two-dimensional image to which information indicating the first region of interest is added and a region-of-interest ultrasound image to which information indicating the second region of interest is added. Further, the display controller 56A also causes the display unit 68 to display the list L (see FIG. 16) of the second regions of interest in the region-of-interest ultrasound image, similarly to the region-of-interest detection unit 59 of the above embodiment.

Note that in the present specific example, a synthesized two-dimensional image is used, but a tomographic image may be used as described above. Furthermore, only one of the first cross-sectional ultrasound image 90 and the second cross-sectional ultrasound image may be used, or a three-dimensional ultrasound image may be used. Furthermore, along with the region-of-interest ultrasound image, or instead of the region-of-interest ultrasound image, information indicating the second region of interest may be configured to be added to the ultrasound image from which the region-of-interest ultrasound image was acquired and displayed.

Therefore, according to the image processing apparatus 18 shown in FIG. 20, by the region-of-interest-related processing, it is possible to easily compare the region of interest between a synthesized two-dimensional image or a tomographic image and an ultrasound image.

In each of the above embodiments, for example, as hardware structures of processing units that execute various types of processing, such as the radiation image acquisition unit 50, the synthesized two-dimensional image generation unit 51, the ultrasound image acquisition unit 52, the image generation unit 53, the position information acquisition unit 54, the depth specifying unit 55, and the display controller 56, various processors shown below can be used. As described above, the various processors include a programmable logic device (PLD) as a processor of which the circuit configuration can be changed after manufacture, such as a field-programmable gate array (FPGA), a dedicated electrical circuit as a processor having a dedicated circuit configuration for executing specific processing such as an application-specific integrated circuit (ASIC), and the like, in addition to the CPU as a general-purpose processor that functions as various processing units by executing software (program).

One processing unit may be configured by one of the various processors, or may be configured by a combination of the same or different types of two or more processors (for example, a combination of a plurality of FPGAs or a combination of the CPU and the FPGA). In addition, a plurality of processing units may be configured by one processor.

As an example in which a plurality of processing units are configured by one processor, first, a form in which one processor is configured by a combination of one or more CPUs and software as typified by a computer, such as a client or a server, and this processor functions as a plurality of processing units can be mentioned. Second, as represented by a system-on-chip (SoC) or the like, a form of using a processor for realizing the function of the entire system including a plurality of processing units with one integrated circuit (IC) chip can be mentioned. In this way, various processing units are configured by one or more of the above-described various processors as hardware structures.

Furthermore, as the hardware structure of the various processors, more specifically, an electrical circuit (circuitry) in which circuit elements such as semiconductor elements are combined can be used.

In each of the above-described embodiments, the image processing program 61 has been described as being stored (installed) in advance in the controller 60 of the image processing apparatus 18; however, the present disclosure is not limited thereto. The image processing program 61 may be provided in a form recorded in a recording medium such as a compact disc read-only memory (CD-ROM), a digital versatile disc read-only memory (DVD-ROM), and a universal serial bus (USB) memory. In addition, the image processing program 61 may be configured to be downloaded from an external device via a network.

In addition, the configurations and operations of the image capturing system 1, the radiography system 2, the mammography apparatus 10, the ultrasonography apparatus 16, the image processing apparatus 18, and the like described in each of the above-described embodiments are merely examples and it goes without saying that they can be changed according to the situation without departing from the gist of the present invention. Furthermore, it goes without saying that the above-described embodiments may be combined as appropriate.

Regarding the above embodiments, the following supplementary notes are further disclosed.

Supplementary Note 1

An image processing apparatus comprising at least one processor, in which the processor is configured to:

acquire a synthesized two-dimensional image including information in a depth direction of a breast, the synthesized two-dimensional image being a composite image obtained by synthesizing a plurality of radiation images of the breast imaged in a compression state by a compression member;

display the synthesized two-dimensional image;

acquire position information indicating a position in the displayed synthesized two-dimensional image;

acquire a plurality of ultrasound images of the breast imaged in a compression state by the compression member, the compression state which is considered to be the same as that in capturing the radiation image; and display an ultrasound image for display according to the plurality of ultrasound images with depth information indicating a depth of the breast corresponding to the position indicated by the position information added thereto.

Supplementary Note 2

The image processing apparatus according to Supplementary Note 1, in which the ultrasound image for display is any of the plurality of ultrasound images, and is at least one of:

a first cross-sectional ultrasound image that is a cross-sectional image in a direction intersecting an imaging table on which the breast is placed;

a second cross-sectional ultrasound image that is synthesized from the plurality of ultrasound images and is a cross-sectional image in a direction intersecting the imaging table and the first cross-sectional ultrasound image;

a third cross-sectional image that is synthesized from the plurality of ultrasound images and is a cross-sectional image parallel to the imaging table; or a three-dimensional ultrasound image that is synthesized from the plurality of ultrasound images and corresponds to a cross section parallel to the imaging table.

Supplementary Note 3

The image processing apparatus according to Supplementary Note 2, in which the processor is configured to display, as the ultrasound image for display to which the depth information is added, at least one of the third cross-sectional image or the three-dimensional ultrasound image corresponding to a cross section according to a position of the depth of the breast corresponding to the position indicated by the position information.

Supplementary Note 4

The image processing apparatus according to any one of Supplementary Notes 1 to 3, in which the processor is configured to:

detect a first region of interest from the synthesized two-dimensional image;

display, on the synthesized two-dimensional image, first region-of-interest information indicating the first region of interest;

acquire position information indicating a position of the first region of interest;

detect a second region of interest from a region corresponding to a vicinity of the first region of interest in the ultrasound image for display; and display, on the ultrasound image for display, second region-of-interest information indicating the second region of interest.

Supplementary Note 5

The image processing apparatus according to any one of Supplementary Notes 1 to 3, in which the radiation image is a radiation image obtained by tomosynthesis imaging, and the processor is configured to:

acquire a tomographic image obtained by reconstructing the radiation image;

detect a first region of interest from the tomographic image;

display, on the synthesized two-dimensional image, a corresponding region corresponding to the first region of interest;

acquire position information indicating a position of the corresponding region on the synthesized two-dimensional image;

detect a second region of interest from a region corresponding to a vicinity of the first region of interest in the ultrasound image for display according to the position indicated by the position information; and display, on the ultrasound image for display, second region-of-interest information indicating the second region of interest.

Supplementary Note 6

The image processing apparatus according to Supplementary Note 4 or 5, in which the processor is configured to:

in a case in which a plurality of the second regions of interest are detected, display a list of scores indicating a degree of suspicion of each second region of interest; and in a case in which a second region of interest designated from the list is received, display information indicating the received second region of interest on the ultrasound image for display.

Supplementary Note 7

The image processing apparatus according to any one of Supplementary Notes 1 to 6, in which the processor is configured to display a line serving as an indicator at a position corresponding to the depth as the depth information to be added to the ultrasound image for display.

Supplementary Note 8

The image processing apparatus according to any one of Supplementary Notes 1 to 7, in which the processor is configured to:

display a movable cross section line on the synthesized two-dimensional image to designate a position of a cross section; and display the ultrasound image for display representing the cross section designated by the cross section line.

Supplementary Note 9

The image processing apparatus according to any one of Supplementary Notes 1 to 8, in which the processor is configured to:

detect a first region of interest from the synthesized two-dimensional image;

display, on the synthesized two-dimensional image, first region-of-interest information indicating the first region of interest; and acquire a position of the first region of interest as the position information.

Supplementary Note 10

The image processing apparatus according to Supplementary Note 9, in which the processor is configured to:

display, on the synthesized two-dimensional image, a cross section line passing through a centroid position or a maximum density position of the region of interest; and display the ultrasound image for display representing the cross section designated by the cross section line.

Supplementary Note 11

The image processing apparatus according to Supplementary Note 10, in which the processor is configured to display, as the cross section line, two cross section lines with the centroid position or the maximum density position of the region of interest as an intersection.

Supplementary Note 12

The image processing apparatus according to Supplementary Note 9, in which the processor is configured to:

detect a second region of interest from the ultrasound image for display representing a cross section designated by a cross section line; and display, on the ultrasound image for display, second region-of-interest information indicating the detected second region of interest.

Supplementary Note 13

The image processing apparatus according to any one of Supplementary Notes 1 to 12, in which the radiation image is a radiation image obtained by tomosynthesis imaging, and the processor is configured to:

acquire a tomographic image obtained by reconstructing the radiation image;

detect a first region of interest from the tomographic image;

acquire position information indicating a position corresponding to the first region of interest on the synthesized two-dimensional image;

display, on the synthesized two-dimensional image, a cross section line passing through a centroid position or a maximum density position of the first region of interest;

display the ultrasound image for display representing a cross section designated by the cross section line;

detect a second region of interest from the ultrasound image for display; and display, on the ultrasound image for display, second region-of-interest information indicating the second region of interest.

Supplementary Note 14

The image processing apparatus according to Supplementary Note 13, in which the processor is configured to:

in a case in which a plurality of the second regions of interest are detected from the ultrasound image for display, display a list of scores indicating a degree of suspicion of each second region of interest; and in a case in which a second region of interest designated from the list is received, display the second region-of-interest information indicating the received second region of interest on the ultrasound image for display.

Supplementary Note 15

The image processing apparatus according to any one of Supplementary Notes 1 to 14, in which the processor is configured to determine that, in a case in which capturing of the ultrasound image and capturing of the radiation image are continuously performed while the breast is kept in the compression state by the compression member, a compression state of the breast in the capturing of the ultrasound image and a compression state of the breast in the capturing of the radiation image are the same.

Supplementary Note 16

The image processing apparatus according to any one of Supplementary Notes 1 to 15, in which the processor is configured to determine that, in a case in which compression conditions for putting the breast into the compression state are the same, a compression state of the breast in capturing of the ultrasound image and a compression state of the breast in capturing of the radiation image are the same.

Supplementary Note 17

The image processing apparatus according to any one of Supplementary Notes 1 to 16, in which the processor is configured to determine that, in a case in which states of the breast in the compression state are the same, a compression state of the breast in capturing of the ultrasound image and a compression state of the breast in capturing of the radiation image are the same.

Supplementary Note 18

The image processing apparatus according to any one of Supplementary Notes 1 to 17, in which the processor is configured to further determine that, in a case in which a state of the breast itself in capturing of the plurality of ultrasound images and a state of the breast itself in capturing of the radiation image are considered to be the same, a compression state of the breast in the capturing of the ultrasound image and a compression state of the breast in the capturing of the radiation image are the same.

Supplementary Note 19

An image capturing system comprising:

the image processing apparatus according to Supplementary Note 1;

a radiography apparatus; and an ultrasonography apparatus.

Supplementary Note 20

An image processing method executed by a computer, the method comprising:

acquiring a synthesized two-dimensional image including information in a depth direction of a breast, the synthesized two-dimensional image being a composite image obtained by synthesizing a plurality of radiation images of the breast imaged in a compression state by a compression member;

displaying the synthesized two-dimensional image;

acquiring position information indicating a position in the displayed synthesized two-dimensional image;

acquiring a plurality of ultrasound images of the breast imaged in a compression state by the compression member, the compression state which is considered to be the same as that in capturing the radiation image; and displaying an ultrasound image for display according to the plurality of ultrasound images with depth information indicating a depth of the breast corresponding to the position indicated by the position information added thereto.

Supplementary Note 21

An image processing program for causing a computer to execute:

acquiring a synthesized two-dimensional image including information in a depth direction of a breast, the synthesized two-dimensional image being a composite image obtained by synthesizing a plurality of radiation images of the breast imaged in a compression state by a compression member;

displaying the synthesized two-dimensional image;

acquiring position information indicating a position in the displayed synthesized two-dimensional image;

acquiring a plurality of ultrasound images of the breast imaged in a compression state by the compression member, the compression state which is considered to be the same as that in capturing the radiation image; and displaying an ultrasound image for display according to the plurality of ultrasound images with depth information indicating a depth of the breast corresponding to the position indicated by the position information added thereto.

Supplementary Note 22

An image processing apparatus comprising at least one processor, in which the processor is configured to:

acquire a synthesized two-dimensional image of a radiation image of a breast imaged in a compression state by a compression member or a tomographic image reconstructed from the radiation image;

detect a first region of interest from the synthesized two-dimensional image or the tomographic image;

acquire a plurality of ultrasound images of the breast imaged in a compression state by the compression member, the compression state which is considered to be the same as that in capturing the radiation image;

acquire a region-of-interest ultrasound image corresponding to the first region of interest from the plurality of ultrasound images;

detect a second region of interest from the region-of-interest ultrasound image; and display the synthesized two-dimensional image or the tomographic image to which information indicating the first region of interest is added and the region-of-interest ultrasound image to which information indicating the second region of interest is added.

What is claimed is:

1. An image processing apparatus comprising at least one processor, wherein the processor is configured to:

acquire a synthesized two-dimensional image including information in a depth direction of a breast, the synthesized two-dimensional image being a composite image obtained by synthesizing a plurality of radiation images of the breast imaged in a compression state by a compression member;

display the synthesized two-dimensional image;

acquire position information indicating a position in the displayed synthesized two-dimensional image;

acquire a plurality of ultrasound images of the breast imaged in a compression state by the compression member, the compression state which is considered to be the same as that in capturing the radiation image; and display an ultrasound image for display according to the plurality of ultrasound images with depth information indicating a depth of the breast corresponding to the position indicated by the position information added thereto, wherein the ultrasound image for display includes at least a first cross-sectional ultrasound image and a second cross-sectional ultrasound image, and the processor is further configured to display, as the depth information, lines serving as an indicator at a position corresponding to the depth in the first and second cross-sectional ultrasound images, detect a first region of interest from the synthesized two-dimensional image, display, on the synthesized two-dimensional image, first region-of-interest information indicating the first region of interest, acquire a position of the first region of interest as the position information, display, on the synthesized two-dimensional image, a cross section line passing through a centroid position or a maximum density position of the region of interest, and display the ultrasound image for display representing the cross section designated by the cross section line.

2. The image processing apparatus according to claim 1, wherein the ultrasound image for display is any of the plurality of ultrasound images, the first cross-sectional ultrasound image is a cross-sectional image in a direction intersecting an imaging table on which the breast is placed;

the second cross-sectional ultrasound image is synthesized from the plurality of ultrasound images and is a cross-sectional image in a direction intersecting the imaging table and the first cross-sectional ultrasound image; and the ultrasound image for display further includes at least one of:

a third cross-sectional image that is synthesized from the plurality of ultrasound images and is a cross-sectional image parallel to the imaging table; or a three-dimensional ultrasound image that is synthesized from the plurality of ultrasound images and corresponds to a cross section parallel to the imaging table.

3. The image processing apparatus according to claim 2, wherein the processor is configured to display, as the ultrasound image for display to which the depth information is added, at least one of the third cross-sectional image or the three-dimensional ultrasound image corresponding to a cross section according to a position of the depth of the breast corresponding to the position indicated by the position information.

4. The image processing apparatus according to claim 1, wherein the processor is configured to:

detect a first region of interest from the synthesized two-dimensional image;

display, on the synthesized two-dimensional image, first region-of-interest information indicating the first region of interest;

acquire position information indicating a position of the first region of interest;

detect a second region of interest from a region corresponding to a vicinity of the first region of interest in the ultrasound image for display; and display, on the ultrasound image for display, second region-of-interest information indicating the second region of interest.

5. The image processing apparatus according to claim 4, wherein the processor is configured to:
in a case in which a plurality of the second regions of interest are detected, display a list of scores indicating a degree of suspicion of each second region of interest; and
in a case in which a second region of interest designated from the list is received, display information indicating the received second region of interest on the ultrasound image for display.

6. The image processing apparatus according to claim 1, wherein the radiation image is a radiation image obtained by tomosynthesis imaging, and the processor is configured to:
acquire a tomographic image obtained by reconstructing the radiation image;
detect a first region of interest from the tomographic image;
display, on the synthesized two-dimensional image, a corresponding region corresponding to the first region of interest;
acquire position information indicating a position of the corresponding region on the synthesized two-dimensional image;
detect a second region of interest from a region corresponding to a vicinity of the first region of interest in the ultrasound image for display according to the position indicated by the position information; and
display, on the ultrasound image for display, second region-of-interest information indicating the second region of interest.

7. The image processing apparatus according to claim 1, wherein the processor is configured to:
display a movable cross section line on the synthesized two-dimensional image to designate a position of a cross section; and
display the ultrasound image for display representing the cross section designated by the cross section line.

8. The image processing apparatus according to claim 1, wherein the processor is configured to display, as the cross section line, two cross section lines with the centroid position or the maximum density position of the first region of interest as an intersection.

9. The image processing apparatus according to claim 1, wherein the processor is configured to:
detect a second region of interest from the ultrasound image for display representing a cross section designated by a cross section line; and
display, on the ultrasound image for display, second region-of-interest information indicating the detected second region of interest.

10. The image processing apparatus according to claim 1, wherein the radiation image is a radiation image obtained by tomosynthesis imaging, and the processor is configured to:
acquire a tomographic image obtained by reconstructing the radiation image;
detect a first region of interest from the tomographic image;
acquire position information indicating a position corresponding to the first region of interest on the synthesized two-dimensional image;
display, on the synthesized two-dimensional image, a cross section line passing through a centroid position or a maximum density position of the first region of interest;
display the ultrasound image for display representing a cross section designated by the cross section line;
detect a second region of interest from the ultrasound image for display; and
display, on the ultrasound image for display, second region-of-interest information indicating the second region of interest.

11. The image processing apparatus according to claim 10,
wherein the processor is configured to:
in a case in which a plurality of the second regions of interest are detected from the ultrasound image for display, display a list of scores indicating a degree of suspicion of each second region of interest; and
in a case in which a second region of interest designated from the list is received, display the second region-of-interest information indicating the received second region of interest on the ultrasound image for display.

12. The image processing apparatus according to claim 1, wherein the processor is configured to determine that, in a case in which capturing of the ultrasound image and capturing of the radiation image are continuously performed while the breast is kept being compressed by the compression member, the compression state of the breast in the capturing of the ultrasound image and the compression state of the breast in the capturing of the radiation image are the same.

13. The image processing apparatus according to claim 1, wherein the processor is configured to determine that, in a case in which compression conditions for compressing the breast are the same in the capturing the ultrasound image and in the capturing of the radiation image, the compression state of the breast in capturing of the ultrasound image and the compression state of the breast in capturing of the radiation image are the same.

14. The image processing apparatus according to claim 1, wherein the processor is configured to determine that, in a case in which a state of the compressed breast are the same in the capturing the ultrasound image and in the capturing of the radiation image, the compression state of the breast in capturing of the ultrasound image and the compression state of the breast in capturing of the radiation image are the same.

15. The image processing apparatus according to claim 1, wherein the processor is configured to further determine that, in a case in which at least one of a size or a hardness of the breast itself in capturing of the plurality of ultrasound images and in capturing of the radiation image are considered to be the same, the compression state of the breast in the capturing of the ultrasound image and the compression state of the breast in the capturing of the radiation image are the same.

16. An image capturing system comprising:
the image processing apparatus according to claim 1;
a radiography apparatus; and
an ultrasonography apparatus.

17. An image processing method executed by a computer, the method comprising:
acquiring a synthesized two-dimensional image including information in a depth direction of a breast, the synthesized two-dimensional image being a composite image obtained by synthesizing a plurality of radiation images of the breast imaged in a compression state by a compression member;

displaying the synthesized two-dimensional image;

acquiring position information indicating a position in the displayed synthesized two-dimensional image;

acquiring a plurality of ultrasound images of the breast imaged in a compression state by the compression member, the compression state which is considered to be the same as that in capturing the radiation image; and displaying an ultrasound image for display according to the plurality of ultrasound images with depth information indicating a depth of the breast corresponding to the position indicated by the position information added thereto, wherein the ultrasound image for display includes at least a first cross-sectional ultrasound image and a second cross-sectional ultrasound image, and the method further comprises displaying, as the depth information, lines serving as an indicator at a position corresponding to the depth in the first and second cross-sectional ultrasound images, detecting a first region of interest from the synthesized two-dimensional image, displaying, on the synthesized two-dimensional image, first region-of-interest information indicating the first region of interest, acquiring a position of the first region of interest as the position information, displaying, on the synthesized two-dimensional image, a cross section line passing through a centroid position or a maximum density position of the region of interest, and displaying the ultrasound image for display representing the cross section designated by the cross section line.

18. A non-transitory storage medium storing an image processing program for causing a computer to execute image processing, the image processing comprising:

acquiring a synthesized two-dimensional image including information in a depth direction of a breast, the synthesized two-dimensional image being a composite image obtained by synthesizing a plurality of radiation images of the breast imaged in a compression state by a compression member;

displaying the synthesized two-dimensional image;

acquiring position information indicating a position in the displayed synthesized two-dimensional image;

acquiring a plurality of ultrasound images of the breast imaged in a compression state by the compression member, the compression state which is considered to be the same as that in capturing the radiation image; and displaying an ultrasound image for display according to the plurality of ultrasound images with depth information indicating a depth of the breast corresponding to the position indicated by the position information added thereto, wherein the ultrasound image for display includes at least a first cross-sectional ultrasound image and a second cross-sectional ultrasound image, and the image processing further comprises displaying, as the depth information, lines serving as an indicator at a position corresponding to the depth in the first and second cross-sectional ultrasound images, detecting a first region of interest from the synthesized two-dimensional image, displaying, on the synthesized two-dimensional image, first region-of-interest information indicating the first region of interest, acquiring a position of the first region of interest as the position information, displaying, on the synthesized two-dimensional image, a cross section line passing through a centroid position or a maximum density position of the region of interest, and displaying the ultrasound image for display representing the cross section designated by the cross section line.

* * * * *